US 9,856,480 B2

United States Patent
Yang et al.

(10) Patent No.: US 9,856,480 B2
(45) Date of Patent: Jan. 2, 2018

(54) DNAZYME FOR SILENCING THE EXPRESSION OF EGFR

(71) Applicants: DCB-USA LLC, Wilmington, DE (US); NATIONAL TAIWAN UNIVERSITY, Taipei (TW); ACADEMIA SINICA, Taipei (TW)

(72) Inventors: Pan-Chyr Yang, Taipei (TW); Wei-Yun Lai, Taipei (TW); Konan Peck, Taipei (TW); Cheng-Ju Chang, Taipei (TW); Chi-Yuan Chen, Taipei (TW); Shuenn-Chen Yang, Taipei (TW)

(73) Assignees: National Taiwan University, Taipei (TW); ACADEMIA SINICA, Taipei (TW)

( * ) Notice: Subject to any disclaimer, the term of this patent is extended or adjusted under 35 U.S.C. 154(b) by 0 days.

(21) Appl. No.: 14/760,904

(22) PCT Filed: Jan. 14, 2014

(86) PCT No.: PCT/US2014/011496
§ 371 (c)(1),
(2) Date: Jul. 14, 2015

(87) PCT Pub. No.: WO2014/110577
PCT Pub. Date: Jul. 17, 2014

(65) Prior Publication Data
US 2016/0145625 A1     May 26, 2016

Related U.S. Application Data

(60) Provisional application No. 61/752,117, filed on Jan. 14, 2013.

(51) Int. Cl.
*A61K 48/00* (2006.01)
*C12N 15/11* (2006.01)
(Continued)

(52) U.S. Cl.
CPC ........ *C12N 15/1138* (2013.01); *A61K 31/517* (2013.01); *A61K 31/713* (2013.01);
(Continued)

(58) Field of Classification Search
USPC .......................................... 536/24.5; 514/44
See application file for complete search history.

(56) References Cited

FOREIGN PATENT DOCUMENTS

WO    WO 2012043633    4/2012

OTHER PUBLICATIONS

Cassell et al. (Expert Opinion on Investigational Drugs, Jun. 2010, vol. 19:709-722).*
(Continued)

*Primary Examiner* — Terra C Gibbs
(74) *Attorney, Agent, or Firm* — WPAT, P.C.; Anthony King

(57) ABSTRACT

The invention provides DNAzymes which are capable to silence the expression of EGFR at allele-specific level. These allele-specific DNAzymes against EGFR T790M mutation will knockdown the expression of EGFR T790M mRNA while keeping EGFR wild-type mRNA intact. Hence, these allele-specific DNAzymes against EGFR T790M mutation may overcome T790M-derived TKI resistance accompanied with lower unwanted side effects on normal cells in lung cancer patients.

24 Claims, 35 Drawing Sheets

(Continued)

(51) Int. Cl.
  C07H 21/02    (2006.01)
  C07H 21/04    (2006.01)
  C12N 15/113   (2010.01)
  C07K 14/485   (2006.01)
  A61K 31/517   (2006.01)
  A61K 31/713   (2006.01)
(52) U.S. Cl.
  CPC ...... *C07K 14/485* (2013.01); *C12N 2310/127* (2013.01); *C12N 2310/315* (2013.01); *C12N 2310/33* (2013.01); *C12N 2310/3515* (2013.01); *C12N 2320/31* (2013.01); *C12N 2320/34* (2013.01)

(56) References Cited

OTHER PUBLICATIONS

Pao et al. (PLOS, Mar. 2005 | vol. 2 | Issue 3, pp. 0225-0235).*
Yu et al. (BBRC, 2008 vol. 378:230-234).*
Search report from the European Patent Office dated Aug. 16, 2016 for European application 14737655.2.
Gang Chen et al: "Effect of siRNAs targeting the EGFR T790M mutation in a non-small cell lung cancer cell line resistant to EGFR tyrosine kinase inhibitors and combination with various agents", Biochemical and Bio Physical Research Communications, Academic Press Inc. Orlando, FL, US, vol. 431, No. 3, Dec. 22, 2012, pp. 623-629, XP028980106.
Gang Chen et al: "Targeting the epidermal growth factor receptor in non-small cell lung cancer cells: the effect of combining RNA interference with tyrosine kinase inhibitors or cetuximab", BMC Medicine, Biomed Central Ltd., London, GB, vol. 10, No. 1, 21 Mar. 2012, p. 28, XP021123822.
Wei-Yun Lai et al: "Overcoming EGFR T790M-based Tyrosine Kinase Inhibitor Resistance with an Allele-specific DNAzyme", Molecular Therapy-Nucleic Acids, vol. 3, No. 3, Mar. 4, 2014, p. e150, XP055286687.
Zhang Shuang et al: "Suppression of Epidermal Growth Factor Receptor (EGFR) Expression by Small Hairpin RNA Inhibits the Growth of Human Non-small Cell Lung Cancers Bearing Wild-type and Mutant EGFR", Cancer Investigation, vol. 29, No. 10, Jan. 1, 2011, pp. 701-708, XP008180787.
European patent office search report for application EP 14737655.2 dated Dec. 23, 2016.
Office action and search report dated Oct. 28, 2016 by the Taiwan Intellectual Property Office for corresponding Taiwan application 103106607.
English abstract translation of the office action dated Oct. 28, 2016 by the Taiwan Intellectual Property Office for corresponding Taiwan application 103106607.
Gang Chen et al., Effect of siRNAs targeting the EGFR T790M mutation in a non-small cell lung cancer cell line resistant to EGFR tyrosine kinase inhibitors and combination with various agents, Biochem Biophys Res Commun. Feb. 15, 2013;431(3):623-629.
Xu, ZhiJie et al., Use of DNAzymes for cancer research and therapy, Chinese Science Bulletin, vol. 57, Issue 26, pp. 3404-3408.
Andre Cassell et al., Investigational EGFR-targeted therapy in head and neck squamous cell carcimoma, Expert Opin Investig Drugs. Jun. 2010;19(6):709-722.
Masaki Takahashi et al., Specific inhibition of tumor cells by oncogenic EGFR specific silencing by RNA interference, PLoS One. Aug. 8, 2013;8(8):e73214.
Raffaella Sordella et al., Gefitinib-sensitizing EGFR mutations in lung cancer activate anti-apoptotic pathways, Science. Aug. 20, 2004;305(5687):1163-1167.

* cited by examiner

A

EGFR_wild-type mRNA (SEQ ID NO: 29)

DzT790M-1 (SEQ ID NO: 1)

EGFR_T790M mRNA (SEQ ID NO: 30)

DzT790M-1 (SEQ ID NO: 1)

B

A (c)

(d)

(a)

(b)

(c)

DNAZYME FOR SILENCING THE
EXPRESSION OF EGFR

FIELD OF THE INVENTION

The invention relates to a DNAzyme for silencing the expression of EGFR. Particularly, the invention relates to an oligonucleotide that specifically hybridizes to EGFR T790M mRNA.

BACKGROUND OF THE INVENTION

The epidermal growth factor receptor (EGFR) is a transmembrane protein expressed in epithelial surfaces. It plays an important physiological role in epithelial repair and regeneration. Epidermal growth factor (EGF) is a peptide secreted by salivary glands and other glands associated with epithelial surfaces that binds to a specific area in the extracellular domain of EGFR. Upon binding it generates a signal that is transmitted inside the cell. The first intracellular event as a result of EGF binding is a conformational change of the intracellular domain of EGFR that allows adenosine 5'-triphosphate (ATP) to enter the so-called tyrosine kinase (TK) domain, a pocket that contains a tyrosine residue, and donate a phosphate group to the tyrosine residue. The intracellular EGFR carrying a phosphorylated tyrosine becomes capable of associating with other intracellular proteins and originates a series of biochemical reactions that propagate downstream through a very complex network. The best known arms of this network are the mitogen-activated protein kinase (MAPK) pathway, which results in tumor cell division upon activation, and the AKT pathway, which results in enhanced cell survival upon activation. The results of EGFR activation are therefore increased cell proliferation and enhanced cellular tolerance to different insults. Many tumors overexpress EGFR compared to adjacent normal tissues or the epithelial surface from which they originate or have a mutated version of EGFR, intrinsically activated or with an enhanced susceptibility to activation. Such overexpression is thought to be one of the many mechanisms by which tumor cells gain a growth advantage, a key characteristic of the malignant phenotype. Consequently, blocking the EGFR signaling pathway is thought to be a rational strategy for the treatment of many human malignancies. There are basically two ways to inhibit upstream the EGFR signaling pathway: 1) preventing EGF and other natural peptide ligands from binding to the extracellular EGFR domain by the use of specific monoclonal antibodies, and 2) preventing ATP and other phosphate donors from entering the TK pocket of the intracellular EGFR domain by the use of small molecules that structurally fit very well into the pocket (i.e., EGFR TK inhibitors such as gefitinib and erlotinib).

Lung cancer is the leading cause of cancer-related death and non-small cell lung cancer (NSCLC) accounts for about 85% of the cases. In one unique subset of NSCLC patients, lung cancer cells harbor activating mutations in epidermal growth factor receptor (EGFR) and addict to aberrant EGFR signaling for cell survival. Among the activating mutations, L858R mutation and LREA deletion in EGFR account for over 90% of drug-sensitive mutations and show increased binding affinity toward tyrosine kinase inhibitors (TKIs) compared to wild-type EGFR. The administration of TKIs successfully induces the intrinsic apoptosis pathways in EGFR-mutant lung cancer cells; however, the dose-limiting side effect such as skin rash and diarrhea are unavoidably triggered by the concurrent inhibition of wild-type EGFR signaling in normal cells. Moreover, despite the success of tyrosine kinase inhibitors at the beginning of NSCLC treatment, the acquired secondary mutation at the gatekeeper residue 790 of EGFR (T790M), which is found in 50% of drug-resistant patients, weakens the interaction between TKIs and EGFR. Dose-limiting toxicity and T790M-derived drug resistance are the main issues in NSCLC treatment which still remain to be solved.

Ribozymes are naturally-occurring RNA molecules that contain catalytic sites, making them more potent agents than antisense oligonucleotides. However, wider use of ribozymes has been hampered by their susceptibility to chemical and enzymatic degradation and restricted target site specificity. A new generation of catalytic nucleic acids has been described containing DNA molecules with catalytic activity for specific RNA sequences. These DNA enzymes exhibit greater catalytic efficiency than hammerhead ribozymes, producing a rate enhancement of approximately 10 million-fold over the spontaneous rate of RNA cleavage, offer greater substrate specificity, are more resistant to chemical and enzymatic degradation, and are far cheaper to synthesize. With rational design, nucleic acid agents able to act on specific mRNAs to silence the expression of target genes at transcript- or allele-specific levels have been exploited by many labs around the world for decades. Among them, DNAzymes have been comprehensively studied to silence various genes with promising results for use as therapeutic agents. The basic structure of DNAzymes consists of a catalytic domain flanked by two substrate binding arms with their sequences complementary to targeted mRNA sequence.

DNAzyme has shown different reaction rate toward different nucleotide composition at mRNA cleavage site. Besides, unlike siRNAs which requires Dicer protein to form RNA-induced silencing complex (RISC) for mRNA cleavage, divalent metal ions such as $Mg^{2+}$ or $Ca^{2+}$, which are abundant in cell cytosol, are sufficient for catalyzing DNAzyme function. Combining these factors together, DNAzymes are cheap, stable, and easy manipulated nucleic acid agents with high efficient mRNA cleavage activity and low non-specific toxicity in cancer therapy.

Gary Beale et al. provide some ribozymes and DNAzymes in inhibiting EGFR expression in A431 cells (Journal of Drug Targeting, August 2003 Vol. 11 (7), pp. 449-456). However, the prior art reference indicates the efficacy of these ribozymes and DNAzymes are less effective in inhibition. Crispin R. Dass et al. published a review article that documents the rise of DNAzymes in the fight against cancer and serves as a forecast for this promising biotechnology in this context (Mol Cancer Ther 2008; 7(2):243-51). US 20120225870 discloses that an anti-ErbB or anti-MET therapeutic may be an enzymatic nucleic acid such as ribozymes, catalytic RNA, enzymatic RNA, catalytic DNA, aptazyme or aptamer-binding ribozyme, regulatable ribozyme, catalytic oligonucleotides, nucleozyme, DNAzyme, RNA enzyme, endoribonuclease, endonuclease, minizyme, leadzyme, oligozyme or DNA enzyme. However, no substantial enzymatic nucleic acid is provided in this reference.

There is still a need to develop DNAzymes which are capable to effectively silence the expression of EGFR or overcome TKI resistance accompanied with lower unwanted side effects.

SUMMARY OF THE INVENTION

The invention provides an oligonucleotide or a modified sequence thereof, which specifically hybridizes to EGFR mutation mRNA so as to inhibit the translation thereof in a cell.

The invention also provides an oligonucleotide or a modified sequence thereof, which specifically hybridizes to EGFR T790M mRNA so as to inhibit the translation thereof in a cell, wherein the oligonucleotide comprises consecutive nucleotides having the sequence selected from the group consisting of SEQ ID NOs:1 to 7.

The invention further provides an oligonucleotide or a modified sequence thereof that specifically hybridizes to EGFR E746-A750 deletion mRNA so as to inhibit the translation thereof in a cell, wherein the oligonucleotide comprises consecutive nucleotides having the sequence of SEQ ID NO: 8.

The invention further provides an oligonucleotide or a modified sequence thereof that specifically hybridizes to EGFR L858R mRNA so as to inhibit the translation thereof in a cell, wherein the oligonucleotide comprises consecutive nucleotides having the sequence selected from the group consisting of SEQ ID NOs: 9-15.

The invention also further provides a vector and a host, which comprises a sequence encoding the oligonucleotide or a modified sequence of the invention.

The invention also further provides a pharmaceutical composition comprising the oligonucleotide or a modified sequence thereof, a vector or a host of the invention and a pharmaceutically acceptable carrier.

The invention also further provides a method of specifically cleaving EGFR mutation mRNA or inhibiting EGFR mutation mRNA expression comprising contacting the mRNA with either of the oligonucleotides or a modified sequence thereof of the invention under conditions permitting the molecule to cleave the mRNA or inhibit the expression of the mRNA.

The invention also further provides a method of treating an EGFR-dependent cancer in a subject, comprising administering an effective amount of an oligonucleotide or a modified sequence thereof of the invention to the subject.

The invention also further provides a method of treating EGFR-dependent cancer in a subject, comprising administering a TKI inhibitor or an EGFR-specific antibody and an oligonucleotide or a modified sequence thereof of the invention to the subject.

DETAILED DESCRIPTION OF THE INVENTION

Figure 1:
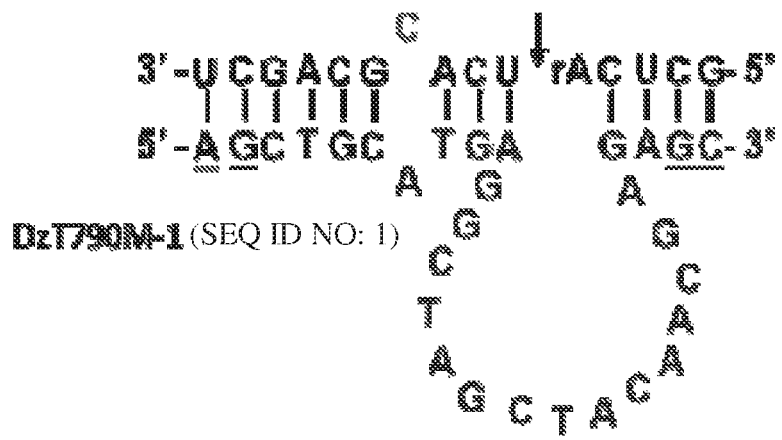
FIG. 1 shows the allele-specific DNAzyme against EGFR T790M mutation.
Figure 1:
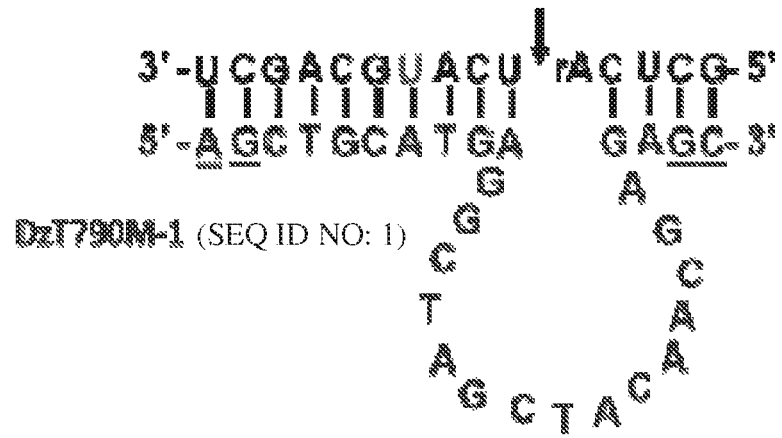
Figure 1:
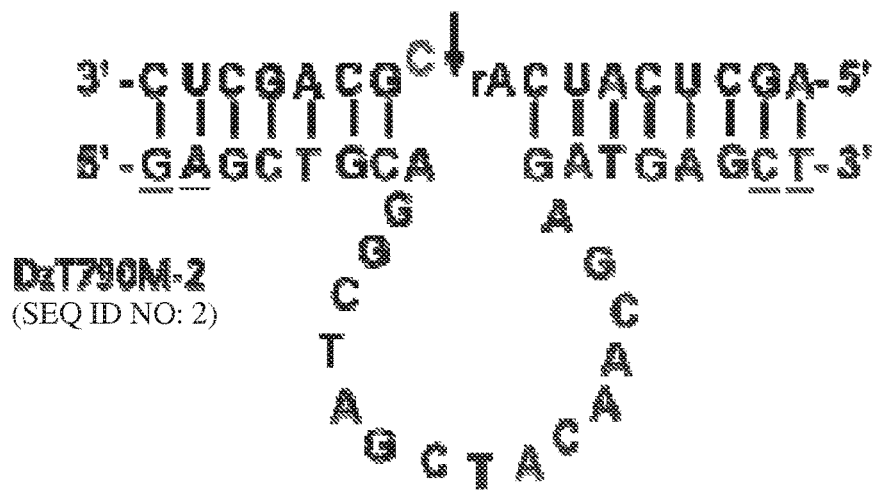
Figure 1:
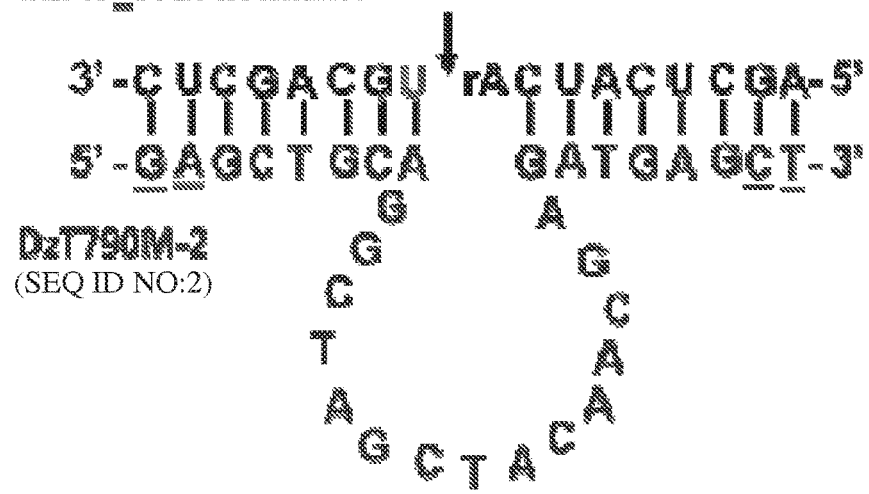

The invention develops DNAzymes which are capable to silence the expression of EGFR at allele-specific level. These allele-specific DNAzymes against EGFR mutation (especially T790M) will knockdown the expression of EGFR mRNA (especially EGFR T790M mRNA) while keeping EGFR wild-type mRNA intact. Hence, these allele-specific DNAzymes against EGFR mutation (especially T790M) may overcome EGFR mutation-derived TKI resistance accompanied with lower unwanted side effects on normal cells in EGFR-dependent cancer (such as NSCLC) patients. Particularly, the DNAzyme of the invention in combination with a TKI inhibitor or an EGFR-specific antibody provides a synergistic effect in treating an EGFR-dependent cancer such as NSCLC.

The terms "a" and "an" refer to one or more than one (i.e., to at least one) of the grammatical object of the article.

The term "nucleic acid" shall include without limitation any nucleic acid, including, without limitation, DNA, RNA, oligonucleotides, or polynucleotides, and analogs or derivatives thereof. The nucleotides that form the nucleic acid may be nucleotide analogs or derivatives thereof. The nucleic acid may incorporate non nucleotides.

The term "nucleotides" shall include without limitation nucleotides and analogs or derivatives thereof. For example, nucleotides may comprise the bases A, C, G, T and U, as well as derivatives thereof. Derivatives of these bases are well known in the art, and are exemplified in PCR Systems, Reagents and Consumables (Perkin Elmer Catalogue 1996-1997, Roche Molecular Systems, Inc., Branchburg, N.J., USA).

The term "nucleic acid enzyme" refers to a nucleic acid molecule that catalyzes a chemical reaction. The nucleic acid enzyme may be covalently linked with one or more other molecules yet remain a nucleic acid enzyme. Examples of other molecules include dyes, quenchers, proteins, and solid supports. The nucleic acid enzyme may be entirely made up of ribonucleotides, deoxyribonucleotides, or a combination of ribo- and deoxyribonucleotides.

The term "DNAzyme" refers to a single-stranded polynucleotide which is capable of cleaving both single and double stranded target sequences.

The term "treatment" or "treating" refers to a treatment of disease in a mammal, including: (a) protecting against the disease, that is, causing the clinical symptoms not to develop; (b) inhibiting the disease, that is, arresting, ameliorating, reducing, or suppressing the development of clinical symptoms; and/or (c) relieving the disease, that is, causing the regression of clinical symptoms. It will be understood by those skilled in the art that in human medicine, it is not always possible to distinguish between "preventing" and "suppressing" since the ultimate inductive event or events may be unknown, latent, or the patient is not ascertained until well after the occurrence of the event or events. Therefore, as used herein the term "prophylaxis" is intended as an element of "treatment" to encompass both "preventing" and "suppressing" as defined herein. The term "protection," as used herein, is meant to include "prophylaxis".

The term "effective amount" means a dosage sufficient to provide treatment for the disorder or disease state being treated. This will vary depending on the patient, the disease and the treatment being effected.

The term "administering" refers to administering according to any of the various methods and delivery systems known to those skilled in the art. The administering can be performed, for example, via implant, transmucosally, transdermally and subcutaneously. In the preferred embodiment, the administering is topical and preferably dermal.

The term "hybridize" refers to the annealing of one single-stranded nucleic acid molecule to another nucleic acid molecule based on sequence complementarity. The propensity for hybridization between nucleic acids depends on the temperature and ionic strength of their milieu, the length of the nucleic acids and the degree of complementarity. The effect of these parameters on hybridization is well known in the art.

The term "inhibit" means to slow, stop or otherwise impede.

The term "pharmaceutically acceptable carrier" refers to any of the various carriers known to those skilled in the art. In one embodiment, the carrier is an alcohol, preferably ethylene glycol. In another embodiment, the carrier is a liposome. The following pharmaceutically acceptable carriers are set forth, in relation to their most commonly associated delivery systems, by way of example, noting the fact that the instant pharmaceutical compositions are preferably delivered dermally.

The term "specifically cleave", when referring to the action of one of the instant catalytic nucleic acid molecules on a target mRNA molecule, shall mean to cleave the target mRNA molecule without cleaving another mRNA molecule lacking a sequence complementary to either of the catalytic nucleic acid molecule's two binding domains.

The term "subject" shall mean any animal, such as a human, a primate, a mouse, a rat, a guinea pig or a rabbit.

The term "vector" shall include, without limitation, a nucleic acid molecule that can be used to stably introduce a specific nucleic acid sequence into the genome of an organism.

The following abbreviations shall have the meanings set forth below: "A" shall mean Adenine; "bp" shall mean base pairs; "C" shall mean Cytosine; "DNA" shall mean deoxyribonucleic acid; "G" shall mean Guanine; "mRNA" shall mean messenger ribonucleic acid; "RNA" shall mean ribonucleic acid; "RT-PCR" shall mean reverse transcriptase polymerase chain reaction; "RY" shall mean purine:pyrimidine; "T" shall mean Thymine; and "U" shall mean Uracil.

In one aspect, the invention provides an oligonucleotide or a modified sequence thereof that specifically hybridizes to EGFR mutation mRNA so as to inhibit the translation thereof in a cell. In one embodiment, the EGFR mutation is EGFR G719, E746-A750 deletion, T790, L858, D761, V765 and T783. In a preferred embodiment, the invention provides an oligonucleotide or a modified sequence thereof that specifically hybridizes to EGFR T790M mRNA so as to inhibit the translation thereof in a cell, wherein the oligonucleotide or a modified sequence thereof comprises consecutive nucleotides having the sequence selected from the group consisting of SEQ ID NOs:1 to 7.

The sequences of SEQ ID NOs: 1 to 7 are listed as follows:

```
                                        (SEQ ID NO: 1)
    DzT790M-1:    AGCTGCATGAGGCTAGCTACAACGAGAGC (SEQ ID NO: 2)
    DzT790M-2:    GAGCTGCAGGCTAGCTACAACGAGATGAGCT (SEQ ID NO: 3)
    DzT1:         CATGAGGCTAGCTACAACGAGAGCTGCACG (SEQ ID NO: 4)
    DzT2:         CTGCATGAGGCTAGCTACAACGAGAGCTGCA (SEQ ID NO: 5)
    DzT3:         GGCATGAGTGTCAGCGACTCGAAGCATGATG (SEQ ID NO: 6)
    DzT4:         AGGGCATGAGTGTCAGCGACTCGAAGCAT (SEQ ID NO: 7)
    DzT5:         TGAGTGTCAGCGACTCGAAGCATGATGAG
```

Preferably, the oligonucleotide has the sequence of SEQ ID NO: 1 or SEQ ID NO:2. More preferably, the oligonucleotide has the sequence of SEQ ID NO: 1.

The above-mentioned embodiment mainly demonstrated the efficacy of allele-specific DNAzyme against T790M to overcome TKI-resistance and reduce toxicity on normal cells. All of the mutations on EGFR mRNA sequences can be designed and functioned in an allele-specific manner. In another embodiment, the invention provides an oligonucleotide or a modified sequence thereof that specifically hybridizes to EGFR E746-A750 deletion mRNA so as to inhibit the translation thereof in a cell, wherein the oligonucleotide or a modified sequence thereof comprises consecutive nucleotides having the sequence of SEQ ID NO: 8. In a further embodiment, the invention provides an oligonucleotide or a modified sequence thereof that specifically hybridizes to EGFR L858R mRNA so as to inhibit the translation thereof in a cell, wherein the oligonucleotide or a modified sequence thereof comprises consecutive nucleotides having the sequence selected from the group consisting of SEQ ID NOs: 9-15.

DNAzyme against EGFR E746-A750 deletion:

DzEGFR_$_{\Delta E746\text{-}A750}$:
(SEQ ID NO: 8)
GGAGATGTGTCAGCTGACTCGAATGATAGCGAC DNAzymes against EGFR L858R mutant:

DzL858R-1:
(SEQ ID NO: 9)
TTTGGCCAGTCAGCGACTCGAACCCAAAAT;

DzL858R-2:
(SEQ ID NO: 10)
GTTTGGCCGTCAGCGACTCGAAGCCCAAAA;

DzL858R-3:
(SEQ ID NO: 11)
GCCCGCCCGTCAGCGACTCGAAAAATCTGT;

DzL858R-4:
(SEQ ID NO: 12)
GGCCCGCCGTCAGCGACTCGAAAAAATCTG;

DzL858R-5:
(SEQ ID NO: 13)
TTGGCCCGGTCAGCGACTCGAACCAAAATC;

DzL858R-6:
(SEQ ID NO: 14)
CAGCAGTTGTCAGCTGACTCGAAGCCCGCCC;
and

DzL858R-7:
(SEQ ID NO: 15)
CCAGCAGTGTCAGCTGACTCGAAGGCCCGCC.

The modified sequence of the invention can be obtained according to the method known in the art. DNAzymes are composed by deoxyribonucleotides which can be easily modified to increase accessibility to targeted RNA, enhance hybridization efficiency toward substrates, improve cleavage activity to complementary sequences, resist degradation against endo- or exo-nucleases in cells and blood stream, and prolong serum half-lives in circulation system. The feasible modifications include introducing modified base on nucleotide structure, modified linkage bonds between nucleotides, and functional groups at the 5'- or 3'-end of DNAzyme. Silverman, Scott K et al. mentioned that chemical modification can be easily introduced to C7 position of the 7-deazaadenine nucleobase and C5 position of the deoxyuriding nucleobase by organic synthesis and these modified bases can be simply incorporated into DNAzyme by suitable polymerases; examples include amine-modified dA, phenol-modified dU, imidazole-modified dU, and pyridine-modified U. (Silverman, S. K. 2008. Catalytic DNA (deoxyribozymes) for synthetic applications-current abilities and future prospects. Chem Commun (Camb):3467-3485.) Schubert, Steffen et al. mentioned that 2'-O-methyl modifications and locked nucleic acid bases comprise a 2'-O, 4'-C methylene bridge that locks in a C3'-endo conformation can enhance DNAzyme cleavage activity. (Schubert, S., Gul, D. C., Grunert, H. P., Zeichhardt, H., Erdmann, V. A., and Kurreck, J. 2003. RNA cleaving '10-23' DNAzymes with enhanced stability and activity. *Nucleic Acids Res* 31:5982-5992.) Furthermore, phosphorothioate bonds between nucleotides, an inverted thymidine at the 3'-end, cholesterol-TEG group at the 3'-end, and different size of PEG moiety at 5'- or 3'-end of DNAzyme can elevate the feasibility in clinical therapy. (Dass, C. R., Choong, P. F., and Khachigian, L. M. 2008. DNAzyme technology and cancer therapy: cleave and let die. *Mol Cancer Ther* 7:243-251.) The invention provides a preferred embodiment with respect to the DNAzyme with phosphorothioate bonds between 3 bases at both ends and cholesterol-TEG group at the 3'-end. In other embodiments, different modifications can be introduced to DNAzyme.

The oligonucleotide of the invention is a DNAzyme capable of downregulating the expression of EGFR mutation mRNA (such as EGFR T790M mRNA, EGFR E746-A750 deletion mRNA and EGFR L858R mRNA) that can specifically cleave its complementary polynucleotide. DNAzymes are single-stranded nucleic acid agents which are capable of cleaving both single and double stranded target sequences (Breaker, R. R. and Joyce, G. Chemistry and Biology 1995; 2:6(55, Santoro, S. W. & Joyce, G. F. Proc. Natl, Acad. Sci. USA 1997; 94:4262). A general model (the "10-23" model) for the DNAzyme has been proposed. Schlosser, Kenny et al. mentioned that "8-17" DNAzyme may achieve cleavage reaction at all di-nucleotide compositions with different reaction rates from 0.0001 to 10/min under in vitro single-turnover conditions. This characteristic allows rational designed "8-17" DNAzyme to silence any sequences they are complemented. In addition, "10-23" DNAzyme could only conduct nucleotide cleavage at purine:pyrimidine junction (i.e. GC, AC, GU/T, AU/T) but not at other di-nucleotide junction. This distinguishing selection ability of "10-23" DNAzyme make it becomes beneficial tool for allele-specific silencing gene expression. (Table 1, Schlosser, K., Gu, J., Lam, J. C., and Li, Y. 2008. In vitro selection of small RNA-cleaving deoxyribozymes that cleave pyrimidine-pyrimidine junctions. *Nucleic Acids Res* 36:4768-4777.) The catalytic domain may optionally contain stem-loop structures in addition to the nucleotides required for catalytic activity. In one embodiment of the catalytic deoxyribonucleic acid molecule, the catalytic domain has the sequence (SEQ ID NO: 16)
GGCTAGCTACAACGA for 10-23 catalytic core sequence, (SEQ ID NO: 17)
GTCAGCGACTCGAA for 8-17 catalytic core sequence, (SEQ ID NO: 18)
GTCAGCTGACTCGAA for 8-17 catalytic core sequence and (SEQ ID NO: 19)
AGGAGGTAGGGGTTCCGCTC for bipartite catalytic core sequence, and cleaves mRNA at the consensus sequence purine:pyrimidine. In a preferred embodiment, cleavage occurs at one or more of the cleavage sites in the EGFR T790M mutation mRNA (shown in FIG. 1B), EGFR E746-A750 deletion mRNA and EGFR L858R mRNA.

Regular DNAzymes have flanked by two substrate-recognition domains of four to twelve deoxyribonucleotides each. These two binding arms provide thermo-stability and substrate specificity between DNAzymes and their complemented targets. For those DNAzymes which binding arms are too short, the interaction strength between DNAzymes and substrate will be too low for cleavage catalysis. On the other hand, the cleavage specificity will be compromised when the binding arm length are too long. Indeed, different nucleotide compositions in the binding arm of DNAzyme will change its hybridization ability and cleavage activity toward its substrate. For regular DNAzyme, the sequences in the binding arm region should perfectly match to the sequences of its targeted substrate. The more mismatches in the binding arm region, the less stability between DNAzyme and the substrate. Moreover, if the mismatches are located near the catalytic core, the catalytic activity will be severely damaged. Recently, Yi, Jz et al. mentioned that introduce the six oligo bulge at the 5'-end of the regular DNAzyme which 12-15 bp away from the catalytic core will increase the efficiency and specificity of the regular DNAzyme. (Yi, J. Z., and Liu, C. Q. 2011. Efficient Silencing of Gene Expression by an ASON-Bulge-DNAzyme Complex. *Plos One* 6.) The most proper binding arm length for cleavage reaction should be examined based on experiments. In an embodiment, different binding arm length and different size of bulge will be introduced to DNAzyme. The invention provides DNAzymes allele-specific silencing EGFR mutation mRNAs. Preferably, the invention provides DNAzymes allele-specific silencing EGFR T790M mRNA; more preferably, the invention provides SEQ ID NOs:1-7. Other DNAzymes with different binding arm length but the same cleavage site toward EGFR T790M mRNA can also be provided. Based on the results of experiments, SEQ ID NO:1 has shown the most effective anti-proliferation effect on T790M-harboring cancer cells. The details of the DNAzymes are described as follows: 10-23 catalytic core sequence:

GGCTAGCTACAACGA. (SEQ ID NO: 16)

8-17 catalytic core sequence:

GTCAGCGACTCGAA. (SEQ ID NO: 17)

| Name | Catalytic core | Binding arm length (Left/right) | Sequences |
|---|---|---|---|
| DzT1 | 10-23 | 4/10 | CATGAGGCTAGCTACAACGAGAGCTGCACG (SEQ ID NO: 3) |
| DzT2 | 10-23 | 8/8 | CTGCATGAGGCTAGCTACAACGAGAGCTGCA (SEQ ID NO: 4) |
| DzT3 | 8-17 | 8/8 | GGCATGAGTGTCAGCGACTCGAAGCATGATG (SEQ ID NO: 5) |
| DzT4 | 8-17 | 10/4 | AGGGCATGAGTGTCAGCGACTCGAAGCAT (SEQ ID NO: 6) |
| DzT5 | 8-17 | 4/10 | TGAGTGTCAGCGACTCGAAGCATGATGAG (SEQ ID NO: 7) |
| DzT790M-1 | 10-23 | 10/4 | AGCTGCATGAGGCTAGCTACAACGAGAGC (SEQ ID NO: 1) |
| DzT790M-2 | 10-23 | 8/8 | GAGCTGCAGGCTAGCTACAACGAGATGAGCT (SEQ ID NO: 2) |

In another aspect, the invention provides a vector which comprises a sequence encoding either of the nucleic acid molecules of the invention. The invention further provides a host comprising the vector therein. This invention still further provides a method of producing either of the nucleic acid molecules comprising culturing a cell having therein a vector comprising a sequence encoding either catalytic nucleic acid molecule under conditions permitting the expression of the nucleic acid molecule by the cell. Methods of culturing cells in order to permit expression and conditions permitting expression are well known in the art. For example see Sambrook et al., "Molecular Cloning: A Laboratory Manual", Second Edition (1989), Cold Spring Harbor Laboratory Press, Cold Spring Harbor, N.Y. Such methods can optionally comprise a further step of recovering the nucleic acid product.

The invention also provides a pharmaceutical composition comprising the oligonucleotide or a modified sequence thereof, vector or host of the invention and a pharmaceutically acceptable carrier.

The compositions of the present invention can be used as single agents (alone) or further in combination(s) with an EGFR TK inhibitor or an EGFR-specific antibody. The EGFR TK inhibitor may include any one or number of the following drugs (including all of them): afatinib (BIBW2992), XL647 (N-(3,4-dichloro-2-fluorophenyl)-6-methoxy-7-(((3aR,6aS)-2-methyloctahydrocyclopenta[c]pyrrol-5-yl)methoxy)quinazolin-4-amine), Neratinib (HKI-272), dacomitinib (PF-00299804), BMS-6690514 ((3R,4R)-4-Amino-1-[[4-[(3-methoxyphenyl)amino]pyrrolo[2,1-f][1,2,4]triazin-5-yl]methyl]piperidin-3-ol), gefitinib and erlotinib and the EGFR-specific antibody may include any one or number of the following drugs (including all of them): cetuximab and panitumumab. Accordingly, the pharmaceutical composition of the invention can further comprise a EGFR TK inhibitor and/or an EGFR-specific antibody.

The pharmaceutical compositions of the invention may be compounded according to conventional pharmaceutical techniques that will be familiar to persons of skill in the art. Physiologically acceptable carriers, excipients and stabilizers are described, for example in Remington's Pharmaceutical Sciences, 20.sup.th Ed. Mack Publishing Co. (2000). The carrier may be provided in a variety of forms depending on the form of preparation desired for administration. The oligonucleotide or a modified sequence thereof, vector, host and composition of the invention can be administered systemically or topically. The term systemic as used herein includes subcutaneous injection, intravenous, intramuscular, intrastemal injection, intravitreal injection, infusion, inhalation, transdermal administration, oral administration, rectal administration and intra-operative instillation. The followings are some examples of the compositions of the invention.

For oral delivery, the excipient or carrier formulation may contain inert customary ingredients or carriers such as sodium citrate or dicalcium phosphate and (a) binders, as for example, carboxymethylcellulose, alignates, gelatin, polyvinylpyrrolidone, sucrose, and acacia, (b) humectants, as for example, glycerol, (c) disintegrating agents, as for example, agar-agar, calcium carbonate, potato or tapioca starch, alginic acid, certain complex silicates, and sodium carbonate, (d) wetting agents, as for example, cetyl alcohol, and glycerol monostearate, (e) adsorbents, as for example, kaolin and bentonite, (f) fillers, such as lactose, starches, saccharides, sucrose, glucose, mannitol, and silicic acid, and (g) lubricants, as for example, magnesium stearate, talc, calcium stearate, solid polyethylene glycols, sodium lauryl sulfate, or mixtures thereof. These and other suitable pharmaceutically acceptable excipients are described in Remington's Pharmaceutical Sciences and in Handbook of Pharmaceutical Excipients, 3.sup.rd edition, Ed. Arthur H. Kibbe (American Pharmaceutical Association, Washington, D.C. 1999.

For parenteral administration, solutions of the oligonucleotide or a modified sequence thereof, vector, host or pharmaceutical composition of the invention in sesame or peanut oil, aqueous propylene glycol, or in sterile aqueous solutions may be employed. Such aqueous solutions should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, the sterile aqueous media employed are all readily available by standard techniques known to those skilled in the art. In intravenous administration, the compounds may be dissolved in appropriate intravenous delivery vehicles containing physiologically compatible substances, such as sterile sodium chloride having a buffered pH compatible with physiologic conditions, e.g. saline. Injectable suspension may also be prepared, in which case appropriate liquid carriers, suspending agents and the like may be employed.

For topical delivery, creams, gels, ointments or aerosols ointments are typically prepared using an oleaginous base, e.g., containing fixed oils or hydrocarbons, such as white petrolatum or mineral oil, or an absorbent base, e.g., consisting of an absorbent anhydrous substance or substances, for example anhydrous lanolin. Following formation of the base, the active ingredients are added in the desired concentration.

Creams generally comprise an oil phase (internal phase) containing typically fixed oils, hydrocarbons, and the like, such as waxes, petrolatum, mineral oil, and the like, and an aqueous phase (continuous phase), comprising water and any water-soluble substances, such as added salts. The two phases are stabilized by use of an emulsifying agent, for example, a surface active agent, such as sodium lauryl sulfate; hydrophilic colloids, such as acacia colloidal clays, beegum, and the like. Upon formation of the emulsion, the active ingredients are added in the desired concentration.

Gels are comprised of a base selected from an oleaginous base, water, or an emulsion-suspension base, as previously described. To the base is added a gelling agent which forms a matrix in the base, increasing its viscosity to a semisolid consistency. Examples of gelling agents are hydroxypropyl cellulose, acrylic acid polymers, and the like. The active ingredients are added to the formulation at the desired concentration at a point preceding addition of the gelling agent.

For rectal delivery, suitable pharmaceutical compositions are, for example, topical preparations, suppositories or enemas. Suppositories are advantageously prepared from fatty emulsions or suspensions.

In a further aspect, the invention relates to a method of specifically cleaving EGFR mutation mRNA comprising contacting the mRNA with either of the oligonucleotides or a modified sequence thereof of the invention under conditions permitting the molecule to cleave the mRNA. In one embodiment, the invention relates to a method of specifically cleaving EGFR T790M mutation mRNA comprising contacting the mRNA with either of the oligonucleotides or a modified sequence thereof of the invention under conditions permitting the molecule to cleave the mRNA. In another embodiment, the invention relates to a method of specifically cleaving EGFR E746-A750 deletion mRNA comprising contacting the mRNA with either of the oligonucleotides or a modified sequence thereof of the invention under conditions permitting the molecule to cleave the mRNA. In another further embodiment, the invention relates to a method of specifically cleaving EGFR L858R mutation mRNA comprising contacting the mRNA with either of the oligonucleotides or a modified sequence thereof of the invention under conditions permitting the molecule to cleave the mRNA. The above-mentioned conditions are well known in the art and include physiological conditions. The invention further provides a method of specifically cleaving EGFR T790M mutation mRNA in a cell, comprising contacting the cell containing the mRNA with either of the oligonucleotides of the invention so as to specifically cleave the EGFR T790M mutation mRNA in the cell. The cell containing EGFR T790M mutation mRNA can be, for example, a naturally occurring cell or a transgenic cell.

This invention further provides a method of specifically inhibiting the expression of EGFR mutation mRNA in a cell that would otherwise express EGFR mutation protein, comprising contacting the cell with either of the oligonucleotides of the invention so as to specifically inhibit the expression of EGFR mutation protein in the cell. In one embodiment, the invention relates to a method of specifically cleaving the expression of EGFR T790M mutation mRNA in a cell that would otherwise express EGFR T790M protein, comprising contacting the cell with either of the oligonucleotides or a modified sequence thereof of the invention so as to specifically inhibit the expression of EGFR T790M protein in the cell. In another embodiment, the invention relates to a method of specifically inhibiting the expression of EGFR E746-A750 deletion mRNA in a cell that would otherwise express EGFR T790M protein, comprising contacting the cell with either of the oligonucleotides or a modified sequence thereof of the invention so as to specifically inhibit the expression of EGFR E746-A750 deletion protein in the cell. In another embodiment, the invention relates to a method of specifically inhibiting the expression of EGFR L858R mutation mRNA in a cell that would otherwise express EGFR T790M protein, comprising contacting the cell with either of the oligonucleotides or a modified sequence thereof of the invention so as to specifically inhibit the expression of EGFR L858R protein in the cell. The invention further provides a method of specifically inhibiting the expression of EGFR T790M protein in a subject's cells comprising administering to the subject an amount of either of the oligonucleotides of the invention effective to specifically inhibit the expression of EGFR T790M protein in the subject's cells.

In a further another aspect, the invention provides a method of treating EGFR-dependent cancer in a subject, comprising administering an effective amount of an oligonucleotide or a modified sequence thereof of the invention to the subject. The invention further provides a method of treating EGFR-dependent cancer in a subject, comprising administering a TKI inhibitor or an EGFR-specific antibody and an oligonucleotide of the invention to the subject. According to the invention, the TKI inhibitor or the EGFR-specific antibody and the oligonucleotide of the invention can be administered concurrently, sequentially or separately. In one embodiment, the EGFR-dependent cancer is a lung cancer; preferably, a NSCLC. According to the invention, the oligonucleotide of the invention can be used in an adjuvant therapy given after surgery, radiation or chemotherapy.

Targeted therapy has been proven as an effective and promising modality for cancer treatment. Several addictive oncogenic pathways involve mutated genes such as EGFR or KRAS. DNAzymes are capable to act on any genes to silence their expression to different extents. Furthermore, with their mRNA sequence specificity, DNAzymes are capable to knock down the expression of the mutated mRNA while keeping the other mRNAs intact. In this case, allele-specific DNAzymes may attack cancer cells without causing side effects on normal cells. Moreover, various studies have shown that the transcript variants of a gene may have opposing roles, and alternative splicing is known to be a key factor in cancer progression. For example, Bcl-x, which is associated with cell survival/apoptosis, has two isoforms, Bcl-xL and Bcl-xS. The longer Bcl-xL isoform acts as an apoptotic inhibitor, whereas the shorter Bcl-xS isoform acts as an apoptotic activator. DNAzymes against a particular splice variant may specifically trigger cell apoptosis without activating cell survival pathway. Furthermore, DNAzyme may serve as a complement in silencing the expression of mRNAs that are difficult to siRNA among the anti-mRNA nucleic acid agents. Recent studies revealed that mRNA knockdown efficiency is dependent on the turnover rate of the mRNA in particular cells. In other words, short lived transcripts are more difficult to be silenced by siRNA. Depending on the substrate sequences and their accessibility, the observed reaction rate constant for 8-17 DNAzyme can be as high as 9.2 $min^{-1}$ whereas the rate constant for RISC can be as high as 1.1 $min^{-1}$. DNAzymes might become surrogates of siRNAs based on their fast kinetic reaction.

The allele-specific DNAzymes of the invention with their mRNA sequence specificity will knock down the expression of a particular mutated mRNA while keeping the other mRNAs intact. These allele-specific DNAzyme may be clinically more effective and better tolerated than traditional tyrosine kinase inhibitors. These allele-specific DNAzymes against EGFR T790M mutation provided in the invention will knockdown the expression of EGFR T790M mRNA while keeping EGFR wild-type mRNA intact. Hence, these allele-specific DNAzymes against EGFR T790M mutation may overcome T790M-derived TKI resistance accompanied with lower unwanted side effects on normal cells in NSCLC patients.

This invention will be better understood by reference to the Examples which follow, but those skilled in the art will readily appreciate that the specific experiments detailed are only illustrative of the invention as described more fully in the claims which follow thereafter.

EXAMPLE

Method and Material

Cell Culture

A549 (EGFR wild-type), CL1-5 (EGFR wild-type), H1975 (EGFR T790M), and CL97 (EGFR T790M) were cultivated at 37° C. with 5% $CO_2$ in RPMI-1640 medium (Gibco BRL, USA) supplemented with 10% (v/v) heat inactivated fetal bovine serum.

Real-Time PCR and Quantitative Real-Time PCR

A549, CL1-5, H1975, or CL97 was seeded onto 6-well at $3 \times 10^5$ cells/well and cultured overnight. Then, cells were separately treated with 100 nM DzControl or DzT790M-1 with lipofectamine 2000 (Invitrogen). After 48 h, total mRNA were extracted from DNAzyme-treated cells by Mestrisol following manufacturer's protocol. cDNA were synthesized by using RT III kit with random hexamers as primers (Invitrogen). The PCR primers were synthesized by Genomics BioSci & Tech (Taipei, Taiwan). The sequences of PCR primers are listed as follows:

```
EGFR:
forward primer:
                                    (SEQ ID NO: 20)
ACCTGCTCAACTGGTGTGTG;

reverse primer:
                                    (SEQ ID NO: 21)
CCAATGCCATCCACTTGATA ACTB:
forward primer:
                                    (SEQ ID NO: 22)
TCCTCCCTGGAGAAGAGCTA;

reverse primer:
                                    (SEQ ID NO: 23)
CGATCCACACGGAGTACTTG
```

The parameters for PCR were: 95° C. for 10 min, then 25 cycles of PCR at 95° C. for 30 s, 60° C. for 30 s, and 72° C. for 60 s. 3% agarose gels were used for electrophoresis of PCR products. The intensity of bands were quantified by Image J. Quantitative RT-PCR was performed on 40 ng total mRNA with the LightCycler 480 system (Roche). The PCR mix contained 5 μl of 2× Probe Master mix, 100 nM of UPL probe (Roche Diagnostics, Penzberg, Germany), 200 nM of forward primer and reverse primer, 0.1 ul RNAseout (Invitrogen), and 0.025 ul RTIII enzyme (Invitrogen) in a total volume of 10 μl. PCR parameters were as follows: 50° C. for 40 min, then 45 cycles of PCR at 95° C. for 10 s, 60° C. for 10 s, and 72° C. for 2 s. Data were analyzed by LC480 software (Roche Diagnostics, Penzberg, Germany). The relative amount of EGFR mRNA was normalized to ACTB mRNA. The sequences of PCR primers are as follows:

```
EGFR:
forward primer:
                                    (SEQ ID NO: 24)
ACATCTCCGAAAGCCAACAA;

reverse primer:
                                    (SEQ ID NO: 25)
CTGCGTGATGAGCTGCAC ACTB:
forward primer:
                                    (SEQ ID NO: 26)
ATTGGCAATGAGCGGTTC;

reverse primer:
                                    (SEQ ID NO: 27)
GGATGCCACAGGACTCCAT
```

Western Immunoblotting

A549, CL1-5, H1975, or CL97 was seeded onto 6-well at $3\times10^5$ cells/well and cultured overnight. Then, cells were separately treated with 100 nM DzControl or DzT790M-1 with lipofectamine 2000 (Invitrogen). The transfected A549 and CL1-5 cells were serum-starved for 24 h and treated with 100 ng/ml of EGF at 37° C. for 15 min. 72 h after transfection, cell were collected for analysis. Cells were washed twice by ice-cold PBS and then total protein was extracted by RIPA buffer with protease inhibitor (Roche). 50 μg of total protein from the supernatants were boiled for 5 min at 95° C. The samples were resolved on 10% SDS-PAGE gel and transferred onto nitrocellulose membranes. EGFR expression and downstream signaling were detected by using primary antibodies specific to human pEGFR (Y1068) (Cell signaling), tEGFR (Santa Cruz), pSTAT3 (Y705) (Cell signaling), tSTAT3 (Cell signaling), pAKT (5473)(Cell signaling), tAKT (Santa Cruz), pERK (T202/Y204) (Cell signaling), tERK (Santa Cruz), and cleaved PARP (Cell signaling) at 1:1000 dilution and β-actin (Santa Cruz) at 1:10000 dilution, respectively. Secondary antibodies against rabbit IgG or mouse IgG was used at 1:5000 dilution. Protein bands on membrane were visualized by exposure to the chemiluminescence substrate.

Cell Proliferation Assay

A549, CL1-5, H1975, or CL97 was seeded onto 6-well and cultured overnight. Then, cells were separately treated with 100 nM DzControl or DzT790M-1 with lipofectamine 2000 (Invitrogen). Cells were trypsinized and counted at 0 h, 24 h, 48 h, or 72 h after transfection.

Apoptosis Assay

H1975 or CL97 was seeded onto 10-cm dish and cultured overnight. Then, cells were separately treated with 100 nM DzControl or DzT790M-1 with lipofectamine 2000 (Invitrogen). After 48 h, cells were collected, double stained by annexin V and PI, and analyzed by flow cytometry following the protocol of Dead cell apoptosis kit from manufacturer (Invitrogen).

In Vivo Tumorigenesis Assay 8-week-old Balb/c Nude mice were subcutaneously inoculated with $2\times10^6$ H1975 cells. After 7 days, mice were randomly divided into two groups consisting of ten mice in each group (DzControl or DzT790M-1). 500 pmoles of DzControl or DzT790M-1 mixed with lipofectamine 2000 were injected intratumorally at frequency of twice per week until completion of the experiments. The sizes of tumor were measured every 3-4 days. All the animal studies were performed according to the protocols approved by the Laboratory Animal Center, Academia Sinica. After the mice were sacrificed, the tumor tissues were excised and fixed by 10% formalin and embedded in paraffin. Xenograft tumor slides were stained for hematoxylin and eosin and analyzed with microscopy.

Statistical Analyses

The data are presented as the means±SD. All Statistical tests having two-sided P<0.05 were considered to be statistically significant.

Example 1 Synthesis of DNAzymes Against EGFR T790M Mutation

Two allele-specific DNAzymes against EGFR T790M mutation (hereinafter referred to DzT790M-1 and DzT790M-2) are 10-23 subtype which comprising 15 deoxyribonucleotides in the catalytic core. The sequences in the binding arm region of DzT790M are complementary to mRNA sequences of EGFR harboring T790M mutation, which is a C to U nucleotide substitution. In DzT790M-1, the mRNA cleavage site is four-nucleotides away from the single nucleotide mutation (Abdelgany, 2005). While the sequences of DzT790M-1 completely match to the mRNA harboring T790M mutation, DzT790M-1 forms one nucleotide mismatch with wild-type mRNA. On the other hand, the allele specificity of DzT790M-2 against T790M mRNA rather than wild-type T790M is based on the different reaction rates of DNAzyme toward different nucleotide junctions. According to the previous study (Cairns, M. J., King, A., and Sun, L. Q. 2003. *Optimisation of the 10-23 DNAzyme-substrate pairing interactions enhanced RNA cleavage activity at purine-cytosine target sites. Nucleic Acids Res* 31:2883-2889), DNAzymes with 10-23 backbone exhibit higher cleavage rate against AU junction compared to AC junction under simulated physiological condition. Hence, DzT790M-2 may exhibit higher cleavage rate toward T790M mRNA compared to wild-type mRNA. Besides, the sequences of control DNAzyme (DzControl) are not complementary to any mRNA in human cells. Phosphorothioate bonds (underlined) are introduced at both end of DNAzyme to resist nuclease degradation. The DNA sequences are listed as follows (FIG. 1).

```
                                       (SEQ ID NO: 28)
DzControl:    CATCGGAGGCTAGCTACAACGAGACAGCTG (SEQ ID NO: 1)
DzT790M-1:    AGCTGCATGAGGCTAGCTACAACGAGAGC (SEQ ID NO: 2)
DzT790M-2:    GAGCTGCAGGCTAGCTACAACGAGATGAGCT
```

Figure 2:
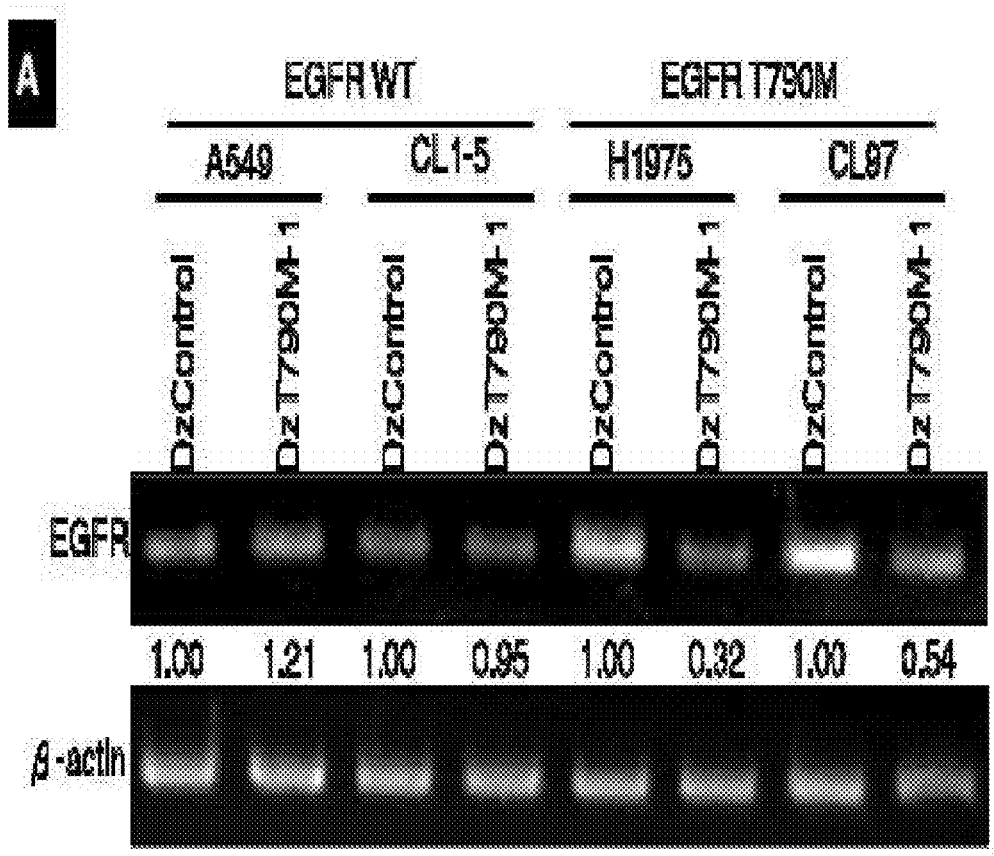
FIG. 2 shows that the allele-specific DNAzyme against EGFR T790M mutation specifically attenuates EGFR mRNA expression level in EGFR T790M-harboring cells.
Figure 2:
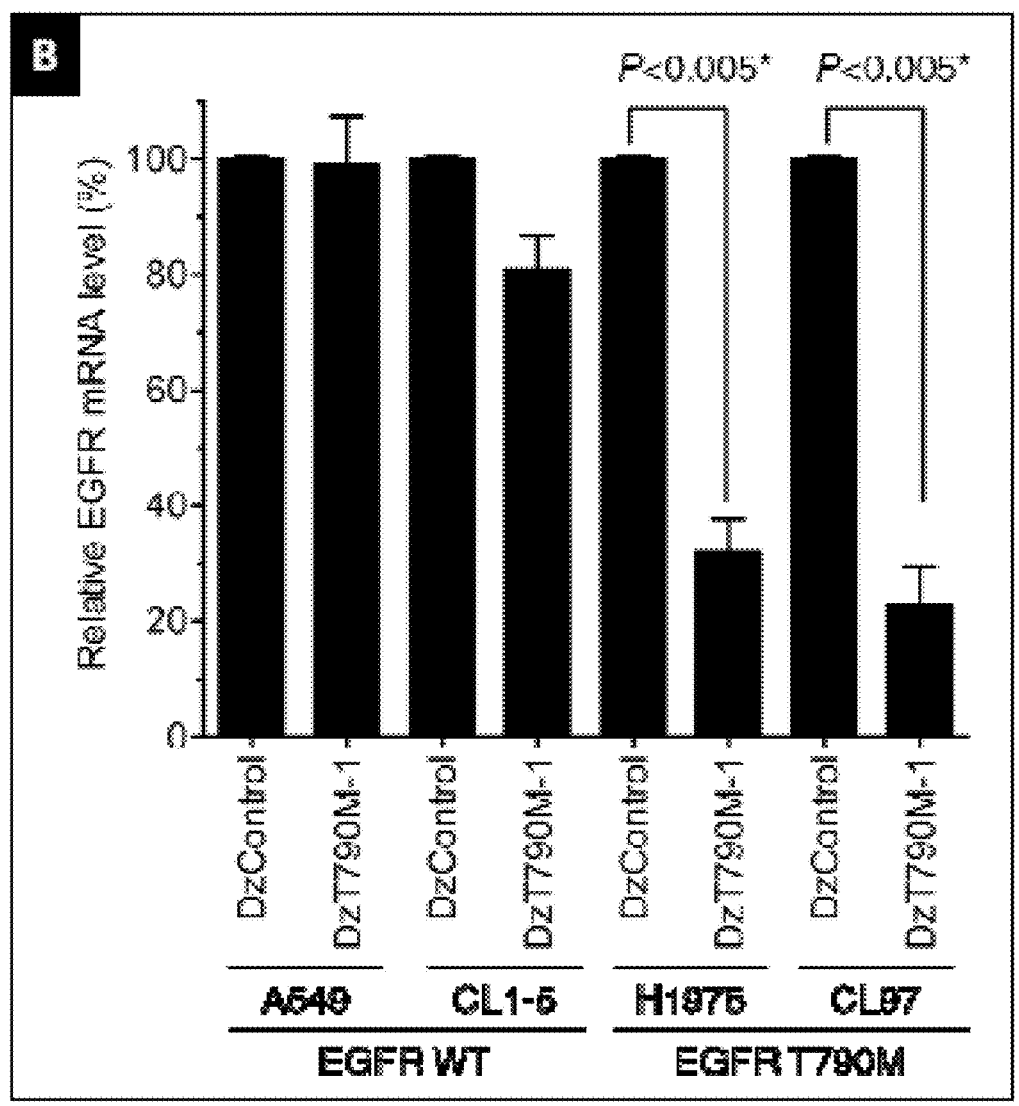

Example 2 Attenuation of EGFR mRNA Expression Level by Allele-Specific DNAzyme Against T790M Mutation To examine the allele selectivity of DzT790M-1, EGFR mRNA knockdown efficiency was detected in two cell lines harboring wild-type EGFR (A549, CL1-5) and two cell lines containing EGFR T790M mutation (H1975, CL97). A549, CL1-5, H1975, or CL97 was seeded onto 6-well at $3\times10^5$ cells/well and cultured overnight. Then, cells were separately treated with 100 nM DzControl or DzT790M-1 with lipofectamine 2000 (Invitrogen). After 48 h, total mRNA was extracted. In FIG. 2A, the results of real-time PCR showed that DzT790M-1 significantly silenced the expression of T790M EGFR mRNA in H1975 and CL97 cells (remained 32% and 54% mRNA expression respectively) while the wild-type EGFR mRNA expression was not inhibited in A549 and CL1-5 cells (remained 121% and 95% mRNA expression respectively). Similar results were founded in quantitative real-time PCR (FIG. 2B). DzT790M-1 knocked down 68.2% and 77.4% T790M EGFR mRNA expression in H1975 and CL97 cells respectively. In contrast, in A549 and CL1-5 cells, only 1.1% and 19.2% wild-type EGFR mRNA expression was affected. DzT790M-1 revealed at least 3.5-fold increased knockdown efficiency toward T790M EGFR mRNA over its wild-type counterpart.

Figure 3:
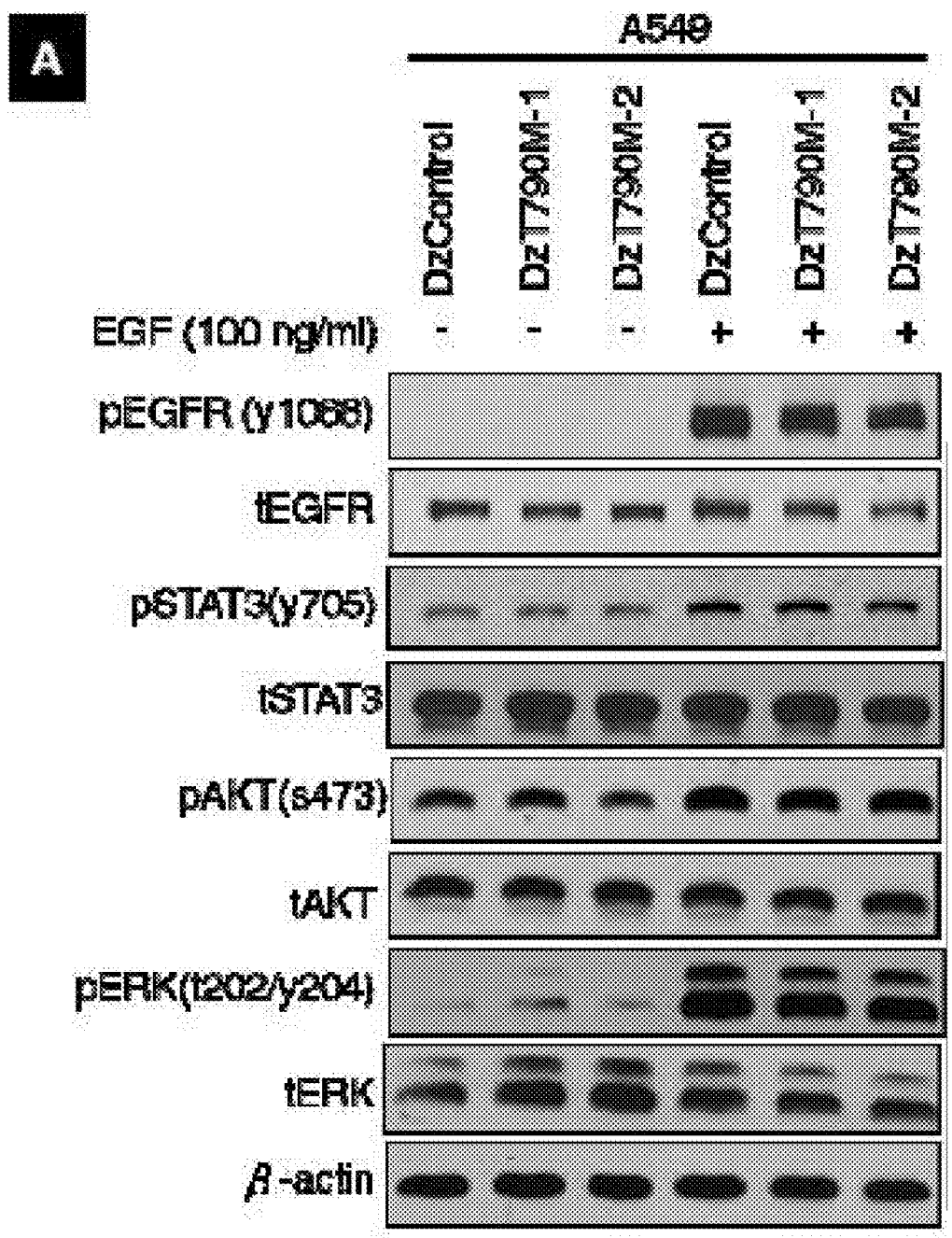
FIG. 3 shows that the allele-specific DNAzyme against EGFR T790M mutation inhibits total EGFR expression and downstream EGFR signaling in EGFR T790M-harboring cells.
Figure 3:
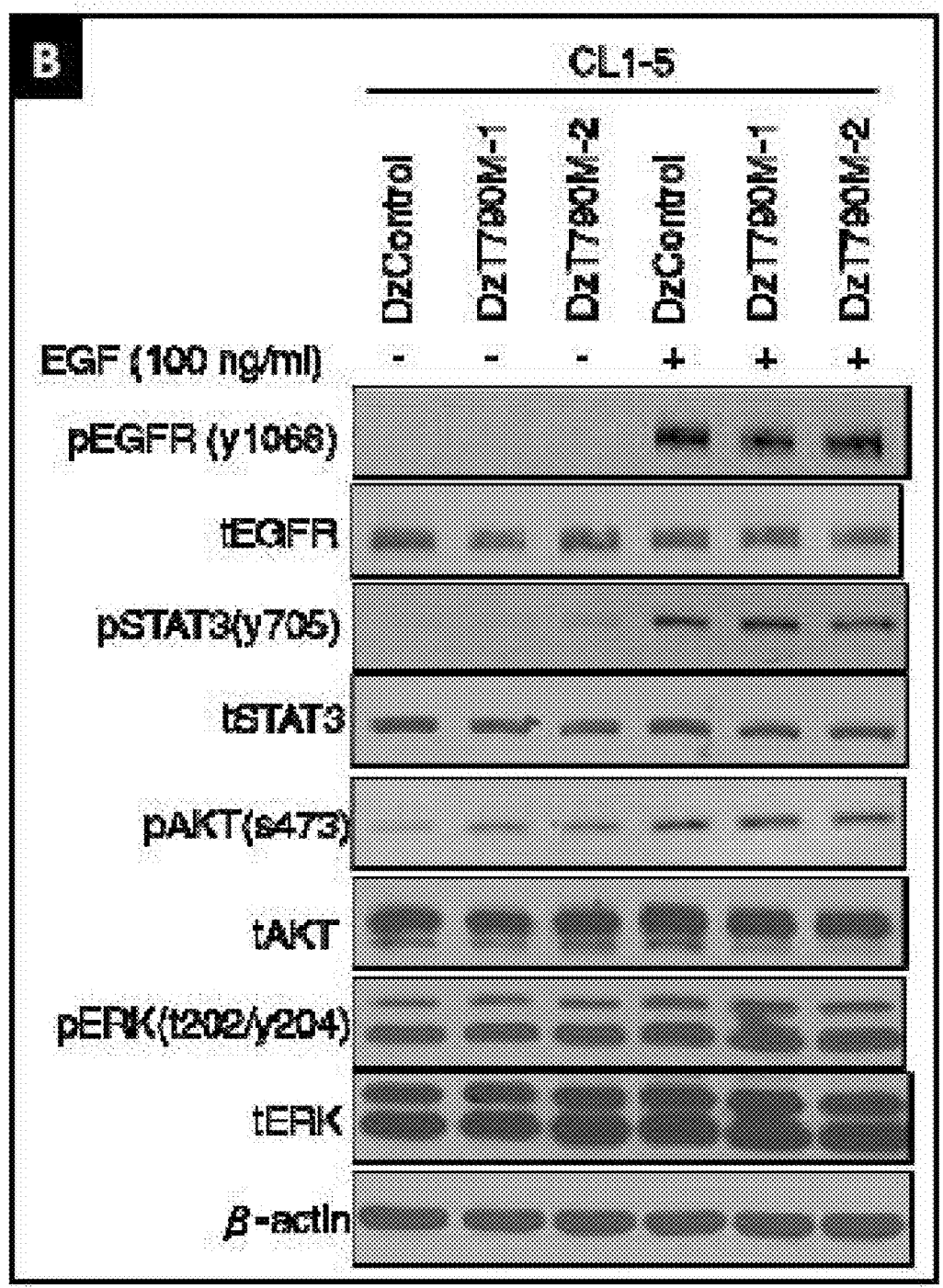
Figure 3:
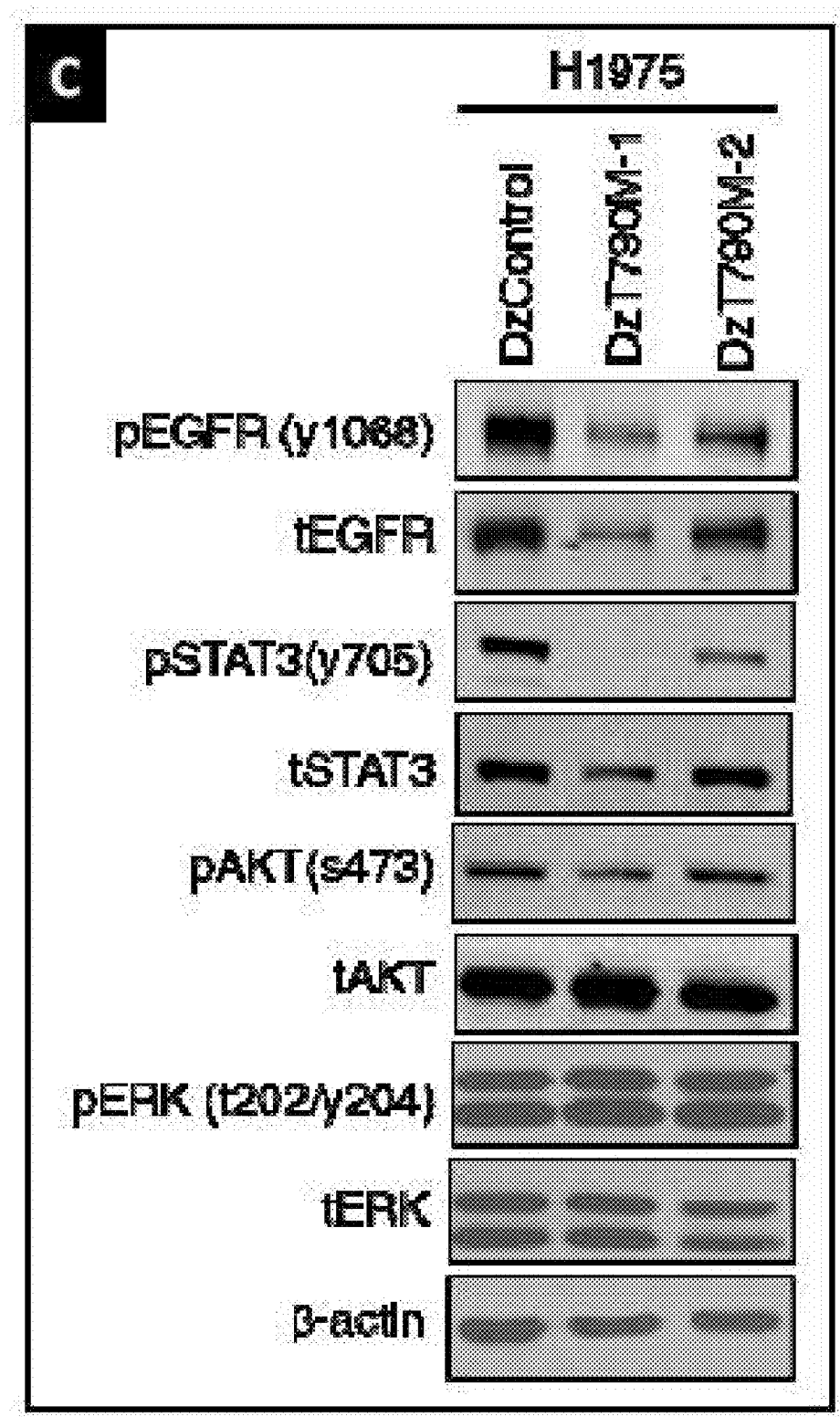
Figure 3:
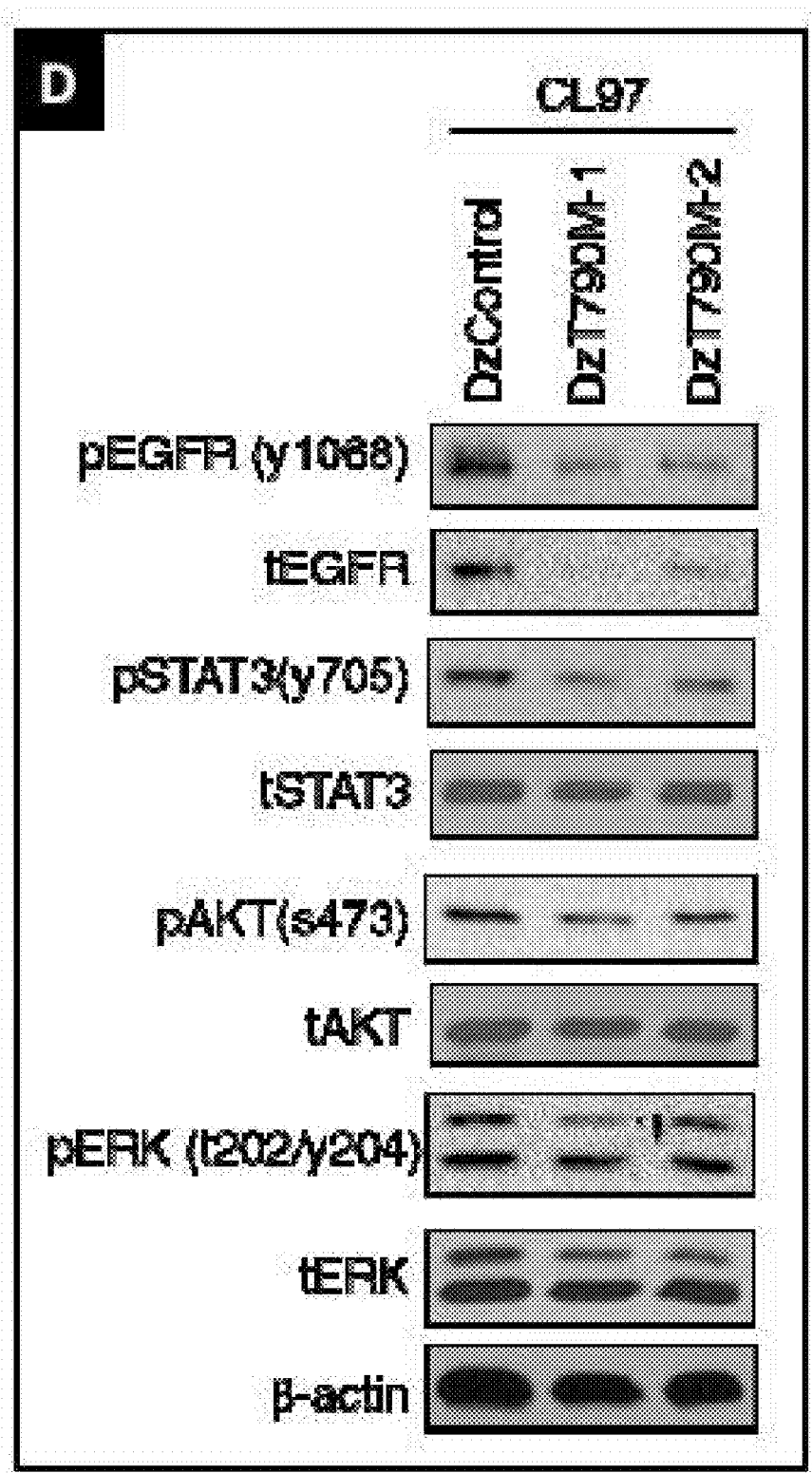

Example 3 Inhibition of Total EGFR Expression and Downstream EGFR Signaling by Allele-Specific DNAzyme Against T790M Mutation EGFR belongs to receptor tyrosine kinases. The binding of its extracellular ligands triggers receptor dimerization, tyrosine residues phosphorylation, and downstream signaling activation including signal transducer and activator of transcription 3 (STAT3), Akt, extracellular signal regulated kinases (ERK), and others. To examine the effects of DzT790M on protein expression level of EGFR and its downstream signaling, western immunoblotting was performed on DzT790M transfected cells. A549, CL1-5, H1975, or CL97 was seeded onto 6-well at $3 \times 10^5$ cells/well and cultured overnight. Then, cells were separately treated with 100 nM DzControl or DzT790M-1 with lipofectamine 2000 (Invitrogen). The transfected A549 and CL1-5 cells were serum-starved for 24 h and treated with 100 ng/ml of EGF at 37° C. for 15 min. 72 h after transfection, cell were collected for analysis. Cells were washed twice by ice-cold PBS and then total protein was extracted by RIPA buffer with protease inhibitor (Roche). In cell lines harboring wild-type EGFR (A549 and CL1-5), the protein level of EGFR did not decreased after DzT790M-1 or DzT790M-2 transfection compared to DzControl group (FIGS. 3A and 3B). Also, activation of downstream STAT3, AKT, and ERK signaling after EGF treatment were not inhibited by DzT790M-1 or DzT790M-2 transfection. On the contrary, DzT790M-1 significantly silenced EGFR protein expression in both EGFR T790M mutant cell lines (H1975 and CL97). In DzT790M-1 transfected H1975 and CL97 cells, decreased phosphorylation of tyrosine residue 1068 on EGFR, tyrosine residue 705 on STAT3, serine residue 473 on AKT, and threonine residue 202/tyrosine residue 204 on ERK (not in H1975 cells) were detected (FIGS. 3C and 3D). Similar results were founded in DzT790M-2 transfected H1975 cells.

Figure 4:
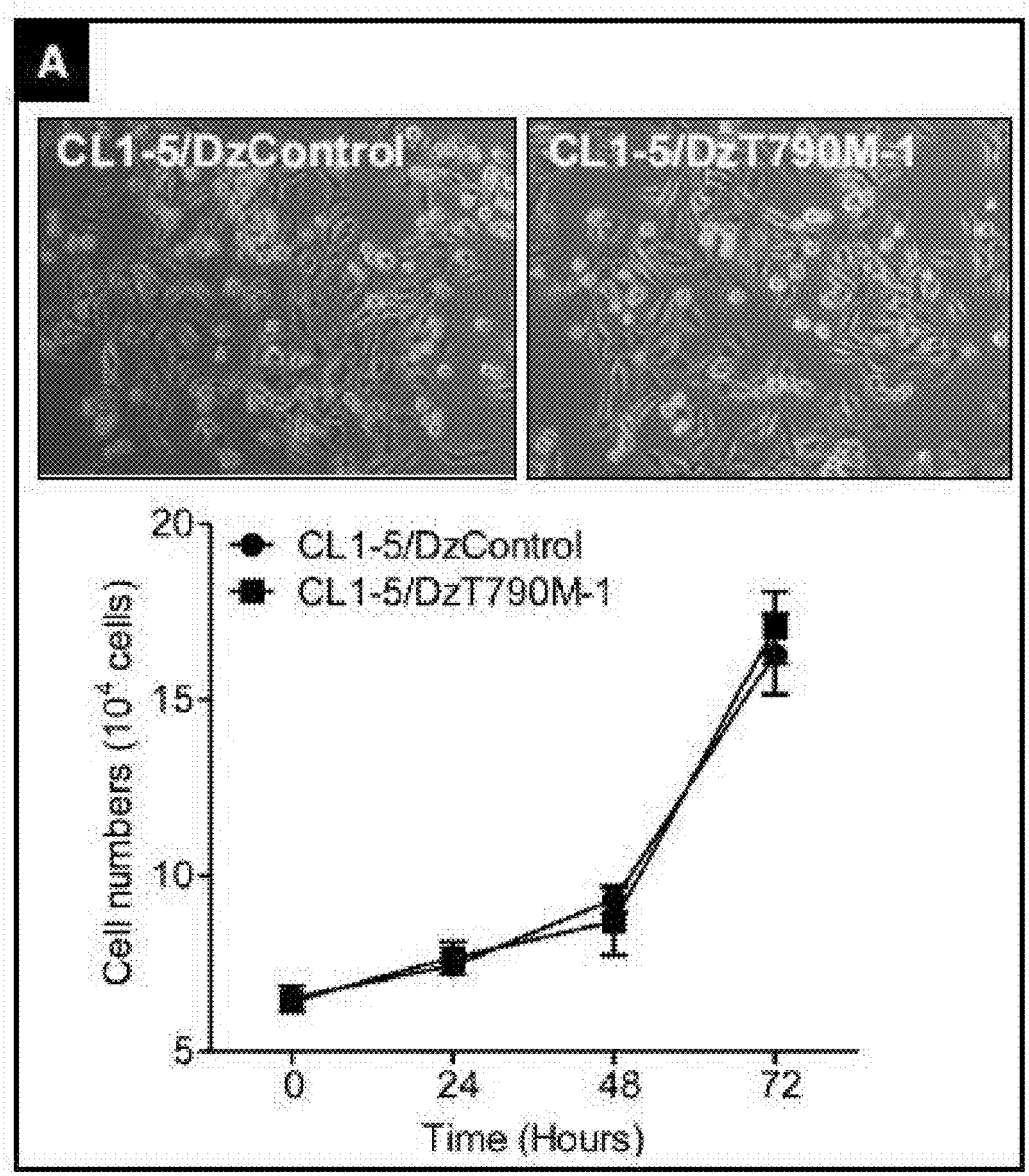
FIG. 4 shows that allele-specific DNAzyme against EGFR T790M mutation induces cell apoptosis in EGFR T790M-harboring cells.
Figure 4:
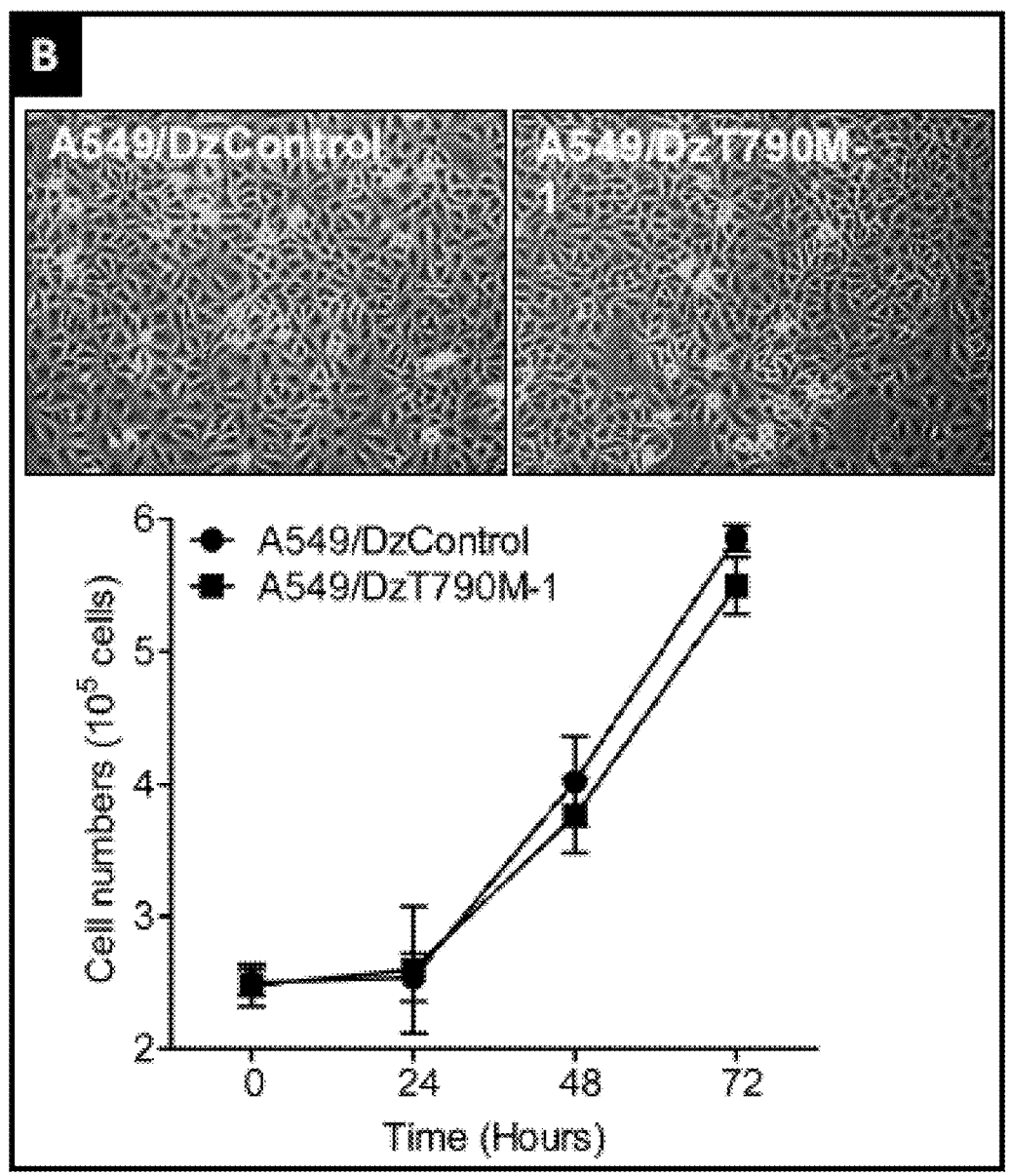
Figure 4:
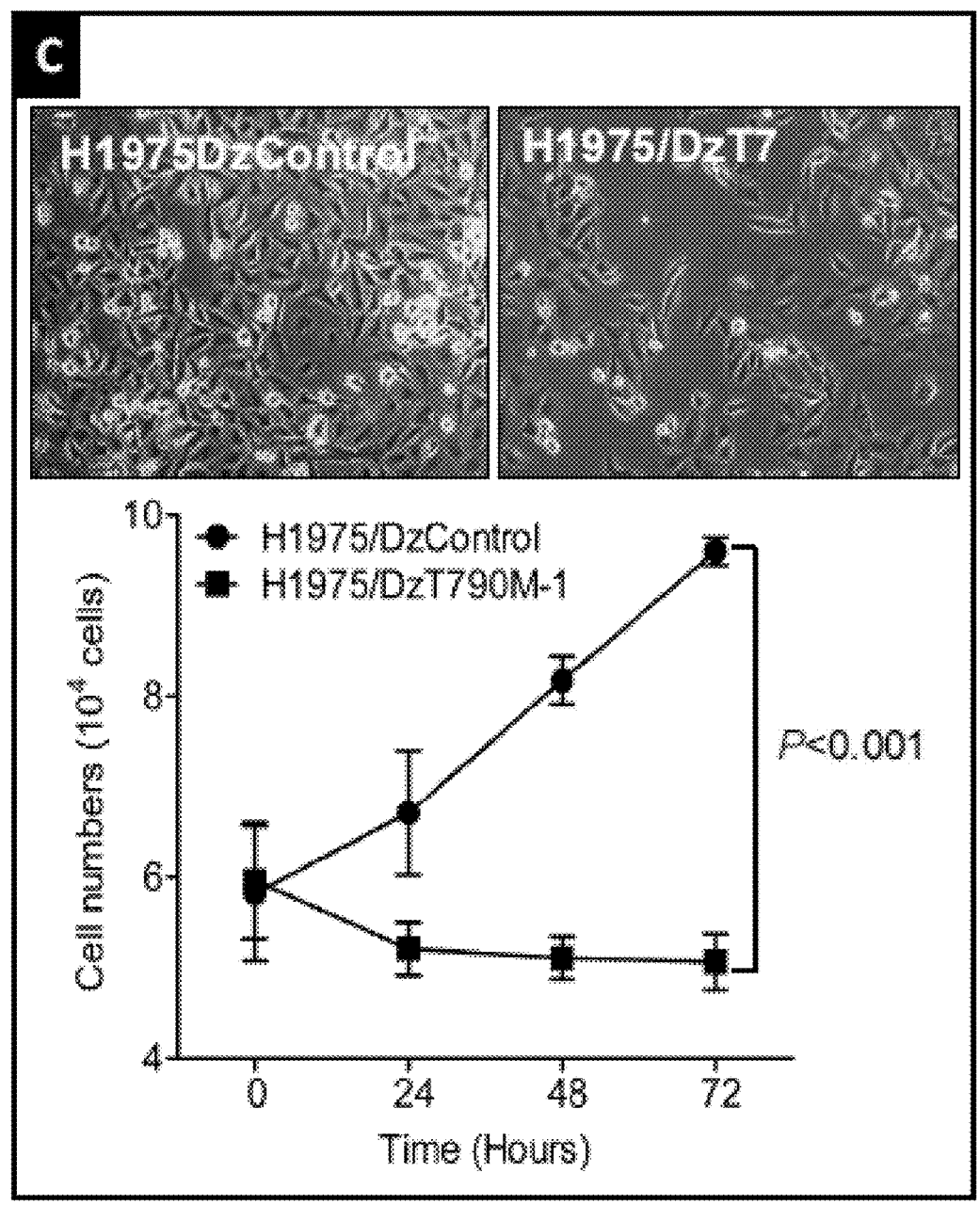
Figure 4:
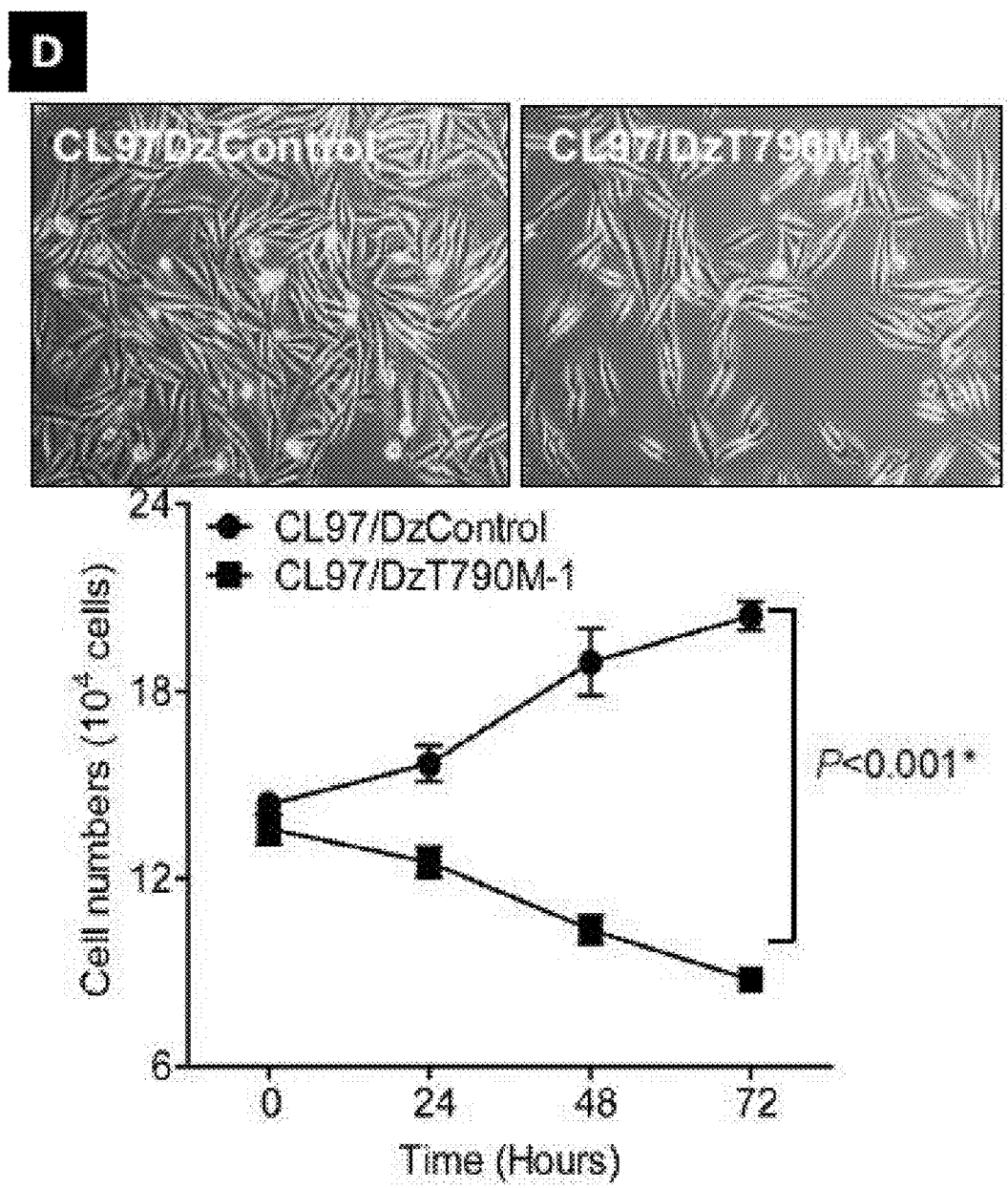
Figure 4:
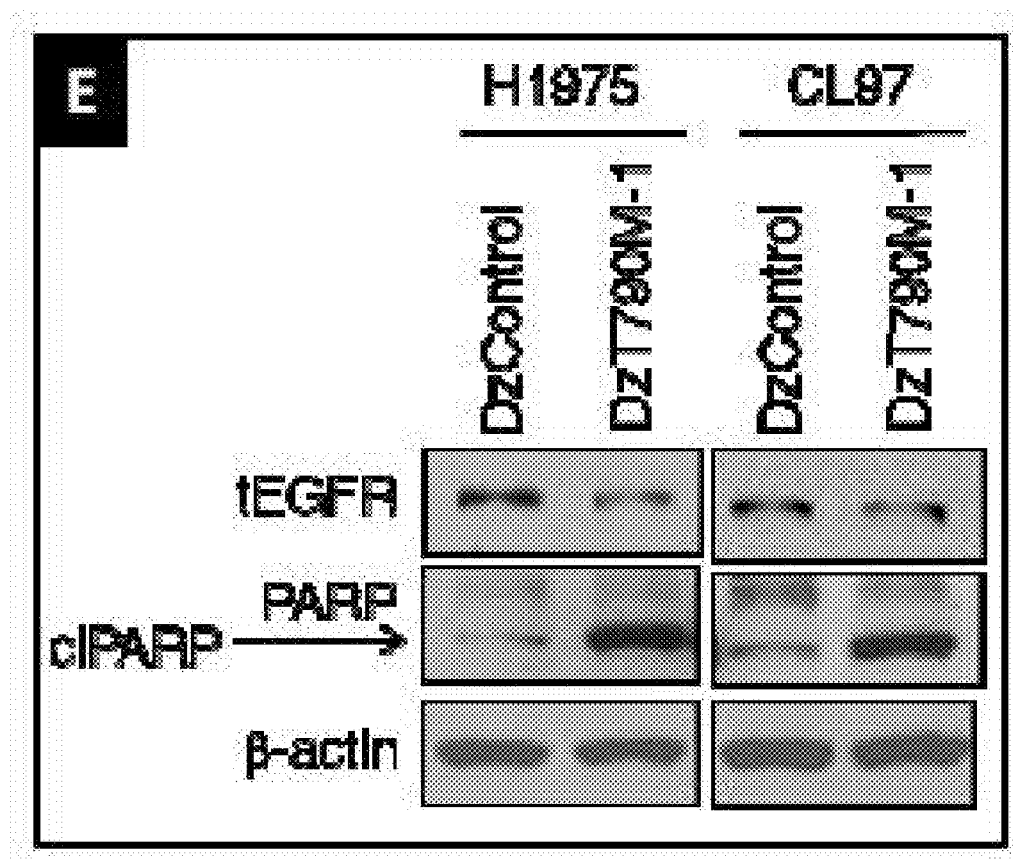
Figure 4:
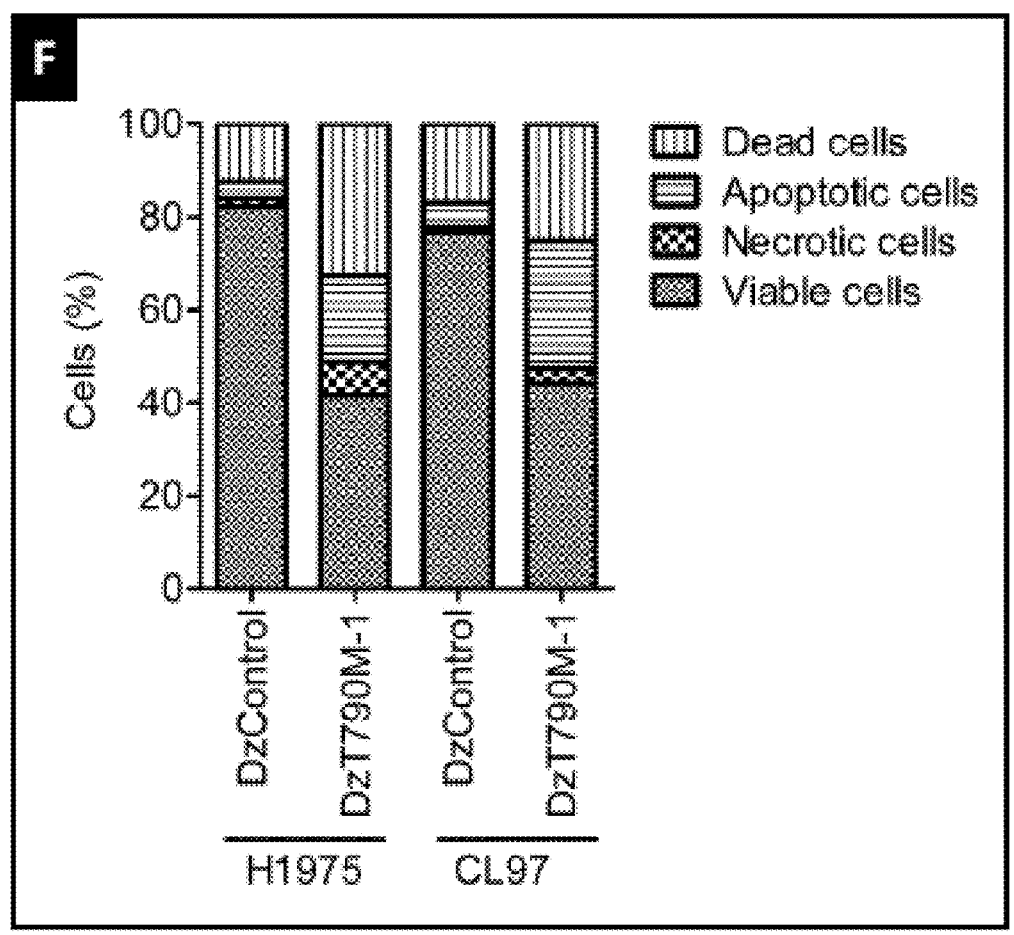

Example 4 Induction of Cell Apoptosis by Allele-Specific DNAzyme Against T790M Mutation EGFR and downstream signaling pathway regulates important cell functions including cell proliferation and survival. In order to examine functional effects of DzT790M-1 on cell survival, the number of cells was counted after DzControl or DzT790M-1 transfection respectively. In A549 and CL1-5 cells (EGFR wild-type), the rate of cell proliferation or the cell number was not different between DzControl and DzT790M-1 transfected group (FIGS. 4A and 4B). In H1975 and CL97 cells (EGFR T790M), DzControl transfected cells were continued to grow after transfection when the number of DzT790M-1 treated cells was reduced (FIGS. 4C and 4D). In order to figure out whether DzT790M-1 treated cells undergoes cell apoptosis, immunoblotting against cleaved form of PARP and immunostaining of annexin V and PI were performed. The cleavage of PARP is caused by increased activity of caspase-3 and serves as a marker for cell apoptosis. The results showed that when DzT790M-1 significantly knockdown the protein expression of EGFR, increased level of cleaved PARP was detected compared to DzControl treated group in H1975 and CL97 cells (FIG. 4E). While only 3.6% of cells underwent apoptosis and 12.4% of cells were dead in DzControl transfected H1975 cells, 18.6% of cells were detected as apoptotic cells and 32.6% of cells were annexin V and PI double positive in DzT790M-1 treated group (FIG. 4F). The results indicated that DzT790M-1 significantly induced cell apoptosis. Similar results were founded in CL97 cells (FIGS. 4E and 4F). Compared to DzControl treated group, DzT790M-1 treatment dramatically increased the percentage of apoptotic cells (from 5.2% to 27.4%) and dead cells (from 17% to 25.1) in whole cell population.

Figure 5:
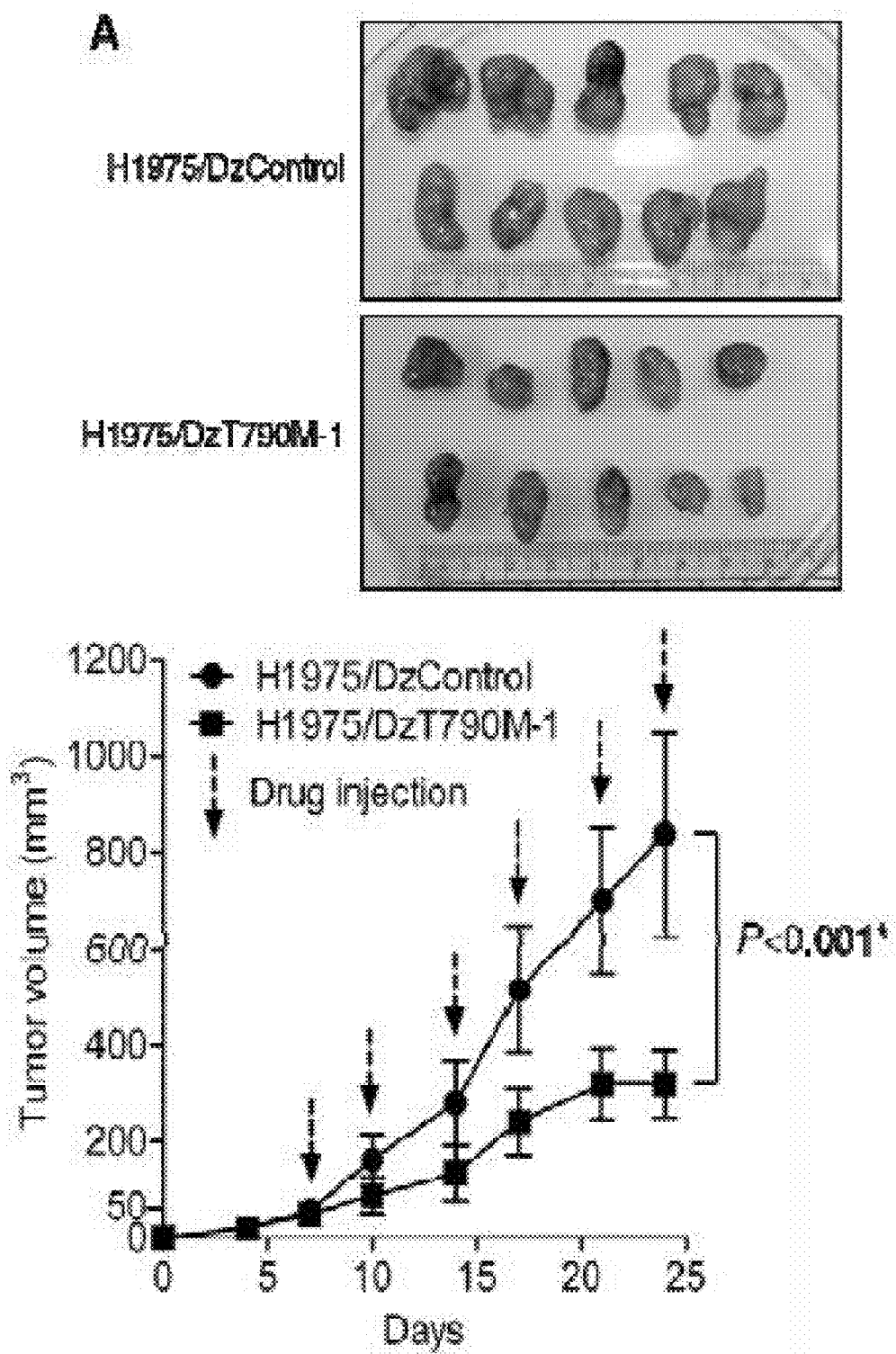
FIG. 5 shows that the allele-specific DNAzyme against EGFR T790M mutation inhibits EGFR T790M-harboring tumor growth in vivo.
Figure 5:
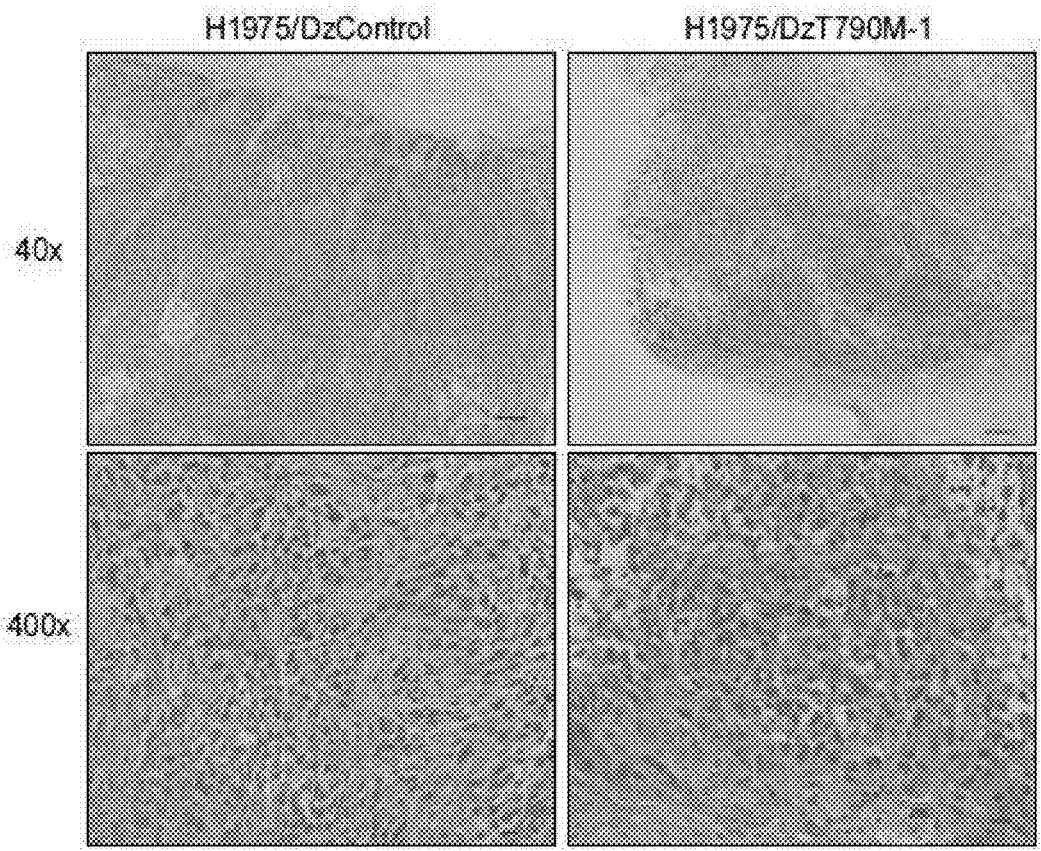
Figure 5:
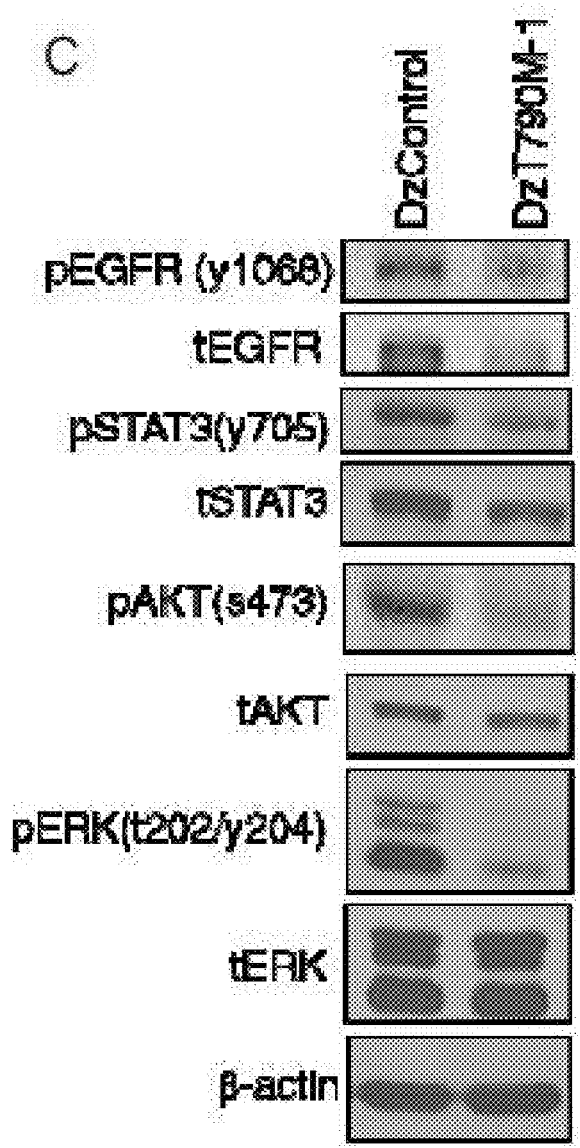

Example 5 Knockdown of EGFR Signaling and Inhibition of Xenograft Tumor Growth by Allele-Specific DNAzyme Against T790M Mutation 8-week-old Balb/c Nude mice were subcutaneously inoculated with $2 \times 10^6$ H1975 cells. After 7 days, mice were randomly divided into two groups consisting of ten mice in each group (DzControl or DzT790M-1). 500 pmoles of DzControl or DzT790M-1 mixed with lipofectamine 2000 were injected intratumorally at frequency of twice per week until completion of the experiments. The sizes of tumor were measured every 3-4 days. The results showed that allele-specific DNAzyme against T790M mutation significantly suppressed tumor growth after intratumorally injection (FIG. 5A). After the mice were sacrificed, the tumor tissues were excised and fixed by 10% formalin and embedded in paraffin. Xenograft tumor slides were stained for hematoxylin and eosin and analyzed with microscopy. Severe necrosis was detected in tumor tissue treated with DzT790M-1 while tumor tissue remained intact in DzControl treated group (FIG. 5B). To assess the effects of DzT790M-1 on EGFR expression and downstream signaling, tumors taken from the Balb/c Nude mice were processed for western blotting. The results showed that total EGFR expression, downstream pEGFR, pSTAT3, pAKT, pERK expression were significantly suppressed in xenograft tumor tissue in vivo (FIG. 5C).

Example 6 Cholesterol Modified Allele-Specific DNAzyme Against T790M Mutation and its Enhanced Anti-Proliferation Effect Materials and Methods
Cell Viability Assay
CL1-5 (EGFR wild-type) or H1975 (EGFR T790M) were seeded in 12-well plates at $1 \times 10^5$ cells/well and cultured overnight. Then, cells were separately treated with 100 nM cholesterol-modified DzControl or DzT790M-1 with lipofectamine 2000 (Invitrogen) for 72 h. Cells were rinsed with PBS buffer for three times and 50 μl MTT solution (0.5 mg/ml) was added. After incubation at 37° C. for 3 h, MTT solution was replaced with DMSO. The cell proliferation was measured by the absorbance at 570 nm with a microplate reader.
Western Blotting
CL1-5 (EGFR wild-type) or H1975 (EGFR T790M) were seeded onto 6-well at $3 \times 10^5$ cells/well and cultured overnight. Then, cells were separately treated with 50 nM cholesterol-modified DzControl or DzT790M-1 with lipofectamine 2000 (Invitrogen). The transfected CL1-5 cells were serum-starved for 24 h and treated with 100 ng/ml of EGF at 37° C. for 15 min. 72 h after transfection, cells were collected for western blotting analysis following the above mentioned procedure. Expression of EGFR and downstream signaling were examined by primary antibodies against human pEGFR (Y1068), tEGFR, pSTAT3 (Y705), tSTAT3, pAKT (S473), tAKT, pERK (T202/Y204), and tERK at 1:1000 dilution and β-actin at 1:10000 dilution, respectively.

Figure 6:
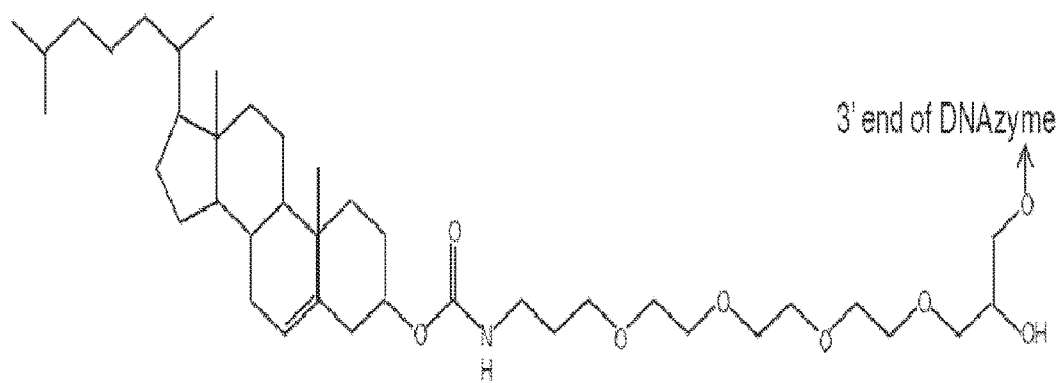
FIG. 6 shows the structure of cholesterol-TEG-modified allele-specific DNAzyme.
Figure 6:
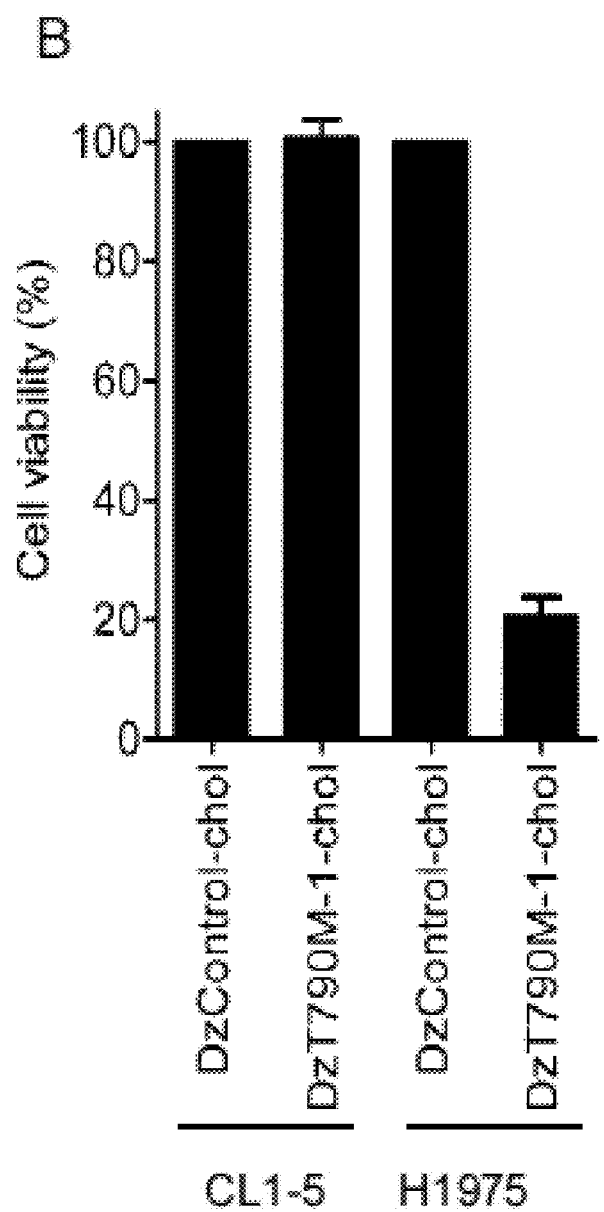
Figure 6:
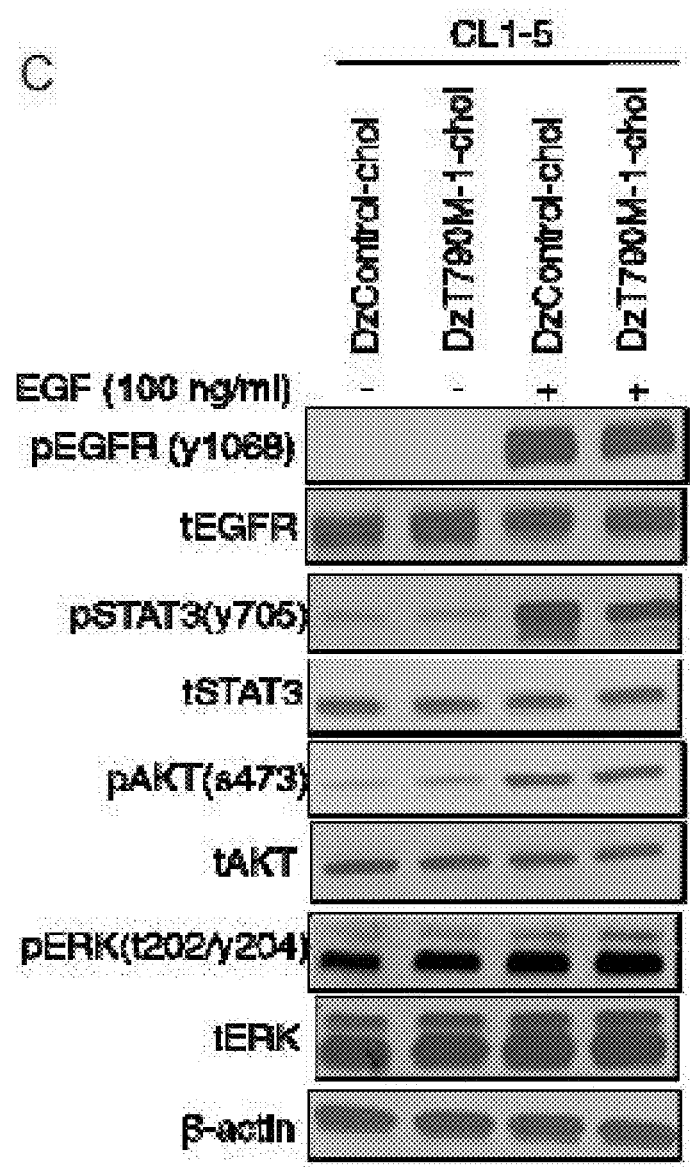
Figure 6:
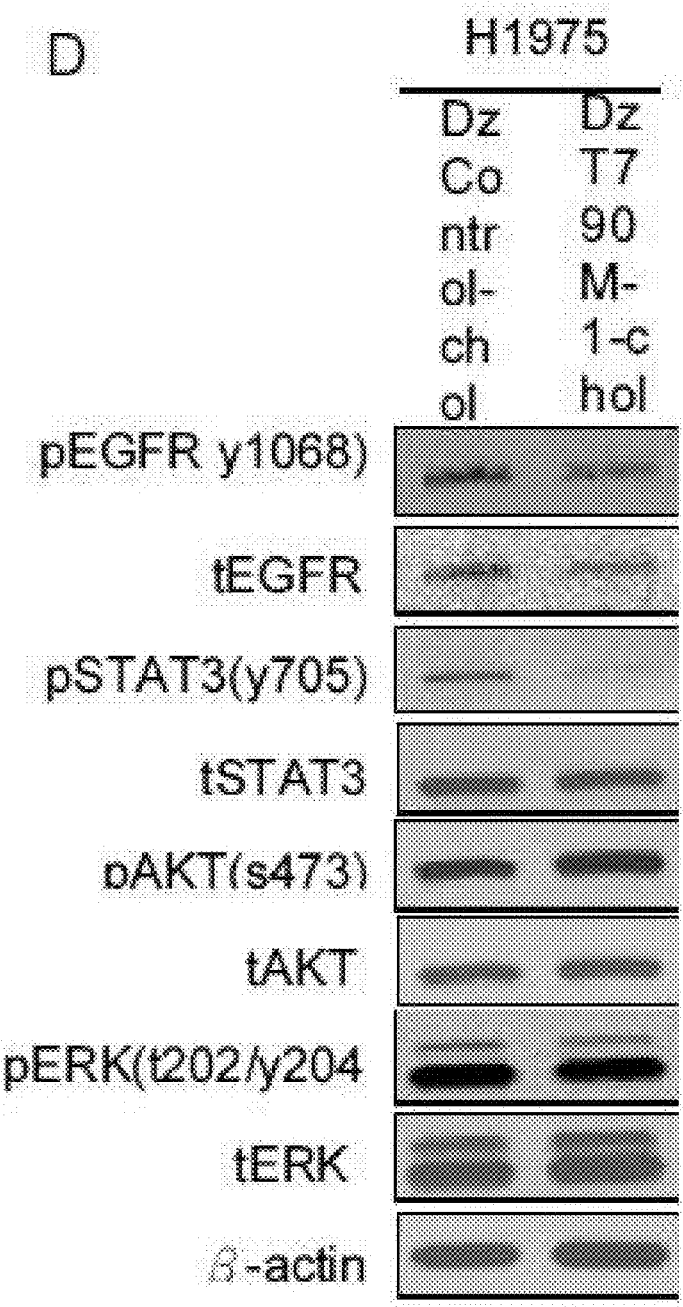

Cholesterol modification on siRNAs or antagomirs has proven to increase endosome escape ability of these therapeutic agents. Hence, we added a cholesterol-TEG group on the 3'-end of DNAzyme (FIG. 6A). By lipofectamine transfection, DNAzyme with cholesterol modification significantly increased the anti-proliferation effect from 50% to 80% in H1975 (EGFR T790M) compared with no cholesterol modification group (FIG. 6B). Also, this cholesterol-modified DNAzyme still remained its allele specificity and did not affect the cell viability in CL1-5 cells (EGFR wild-type) (FIG. 6B). Furthermore, allele-specific inhibition effect on EGFR expression and downstream signaling in T790M-harboring cells but not wild-type-expressing cells can be achieved by half-dose administration of cholesterol-modified DzT790M-1 compared to no cholesterol-modified one (FIGS. 6C and 6D).

Example 7 Combined Treatment of Cholesterol-Modified DzT790M with Afatinib (BIBW2992)

Materials and Methods

H1975 was seeded onto 6-well at 3×10$^5$ cells/well and cultured overnight. Then, cells were separately treated with 50 nM cholesterol-modified DzControl or DzT790M-1 with lipofectamine 2000 (Invitrogen). Simultaneously, DMSO or 100 nM BIBW2992 was added into culture medium. 72 h after transfection, cells were collected for western blotting analysis following the above mentioned procedure. Expression of EGFR and downstream signaling were examined by primary antibodies against human pEGFR(Y1068), tEGFR, pSTAT3 (Y705), tSTAT3, pAKT (S473), tAKT, pERK (T202/Y204), and tERK at 1:1000 dilution and β-actin at 1:10000 dilution, respectively.

Cell Viability Assay

H1975 were seeded in 12-well plates at 1×10$^5$ cells/well and cultured overnight. Then, cells were separately treated with 50 nM cholesterol-modified DzControl or DzT790M-1 with lipofectamine 2000 (Invitrogen) combined with DMSO or 100 nM BIBW2992 for 72 h. Cells were rinsed with PBS buffer for three times and 50 μl MTT solution (0.5 mg/ml) was added. After incubation at 37° C. for 3 h, MTT solution was replaced with DMSO. The cell proliferation was measured by the absorbance at 570 nm with a microplate reader.

In Vivo Tumorigenesis Assay 8-week-old Balb/c Nude mice were subcutaneously inoculated with 2×10$^6$ H1975 cells. After 10 days, mice were randomly divided into four groups consisting of ten mice in each group: (1) DzControl-chol+PBS, (2) DzControl-chol+BIBW2992, (3) DzT790M-1-chol+PBS, and (4) DzT790M-1-chol+BIBW2992. For cholesterol-modified DNAzyme treatment, 500 pmoles of DzControl-chol or DzT790M-1-chol mixed with lipofectamine 2000 were injected intratumorally at frequency of twice per week until completion of the experiments. For BIBW2992 treatment, BIBW2992 was suspended in PBS and administration by oral gavage at 20 mg/per kg mice at frequency of three times per week until completion of the experiments. The sizes of tumor were measured every 3-4 days. All the animal studies were performed according to the protocols approved by the Laboratory Animal Center, Academia Sinica.

Figure 7:
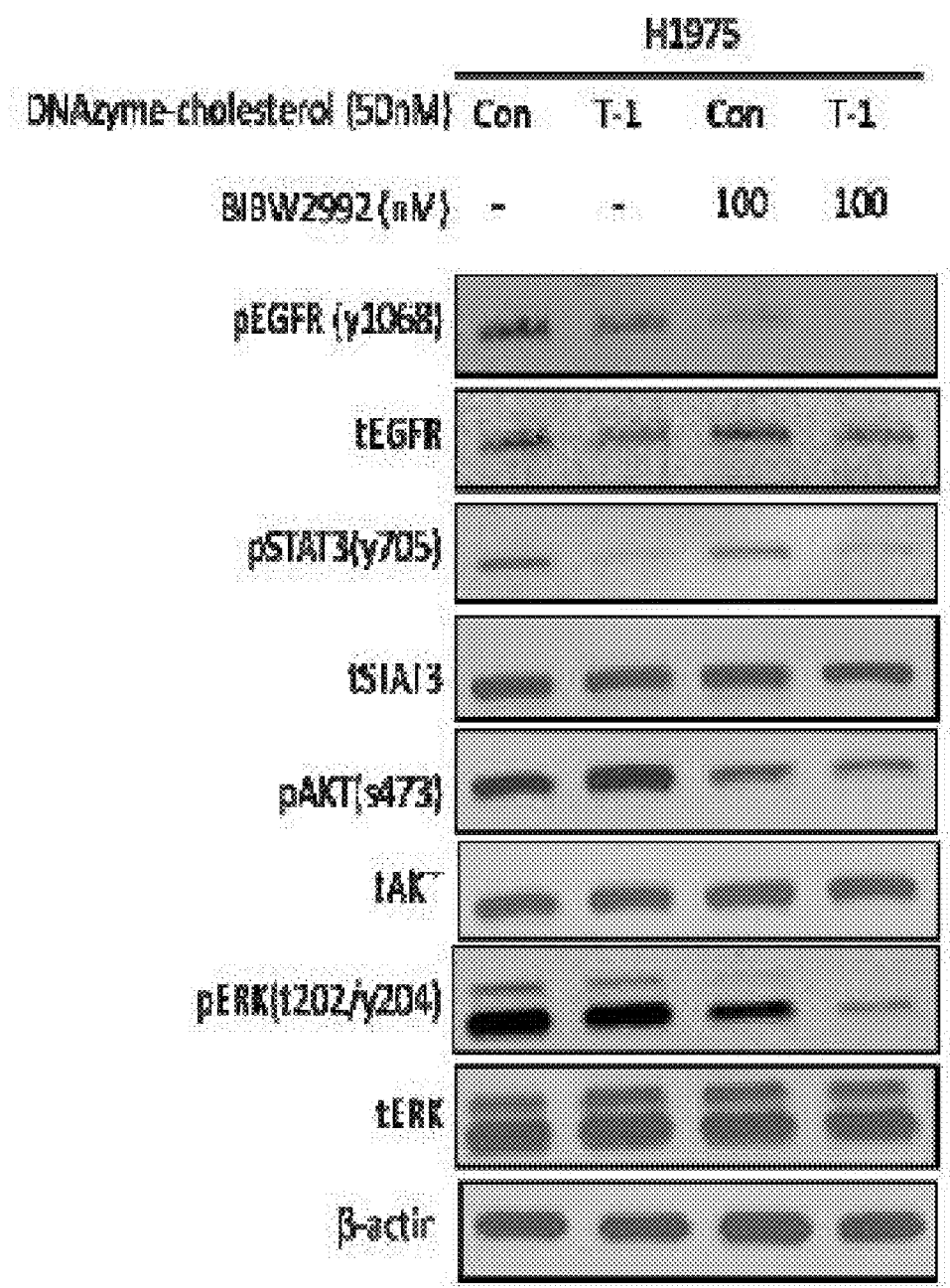
FIG. 7 shows the combination therapy of DNAzyme and Afatinib.
Figure 7:
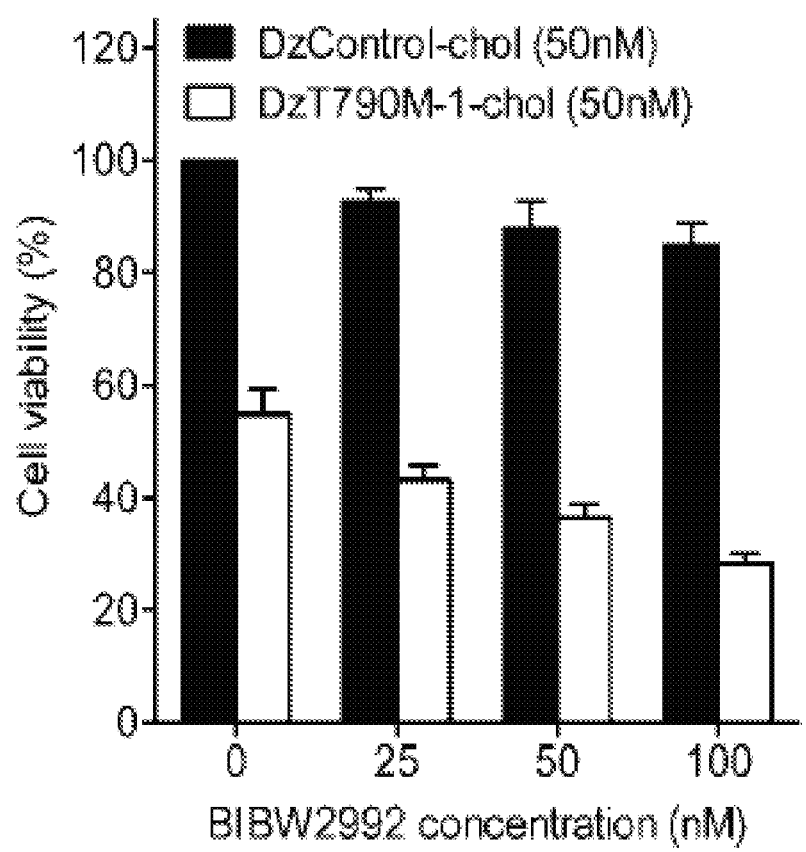
Figure 7:
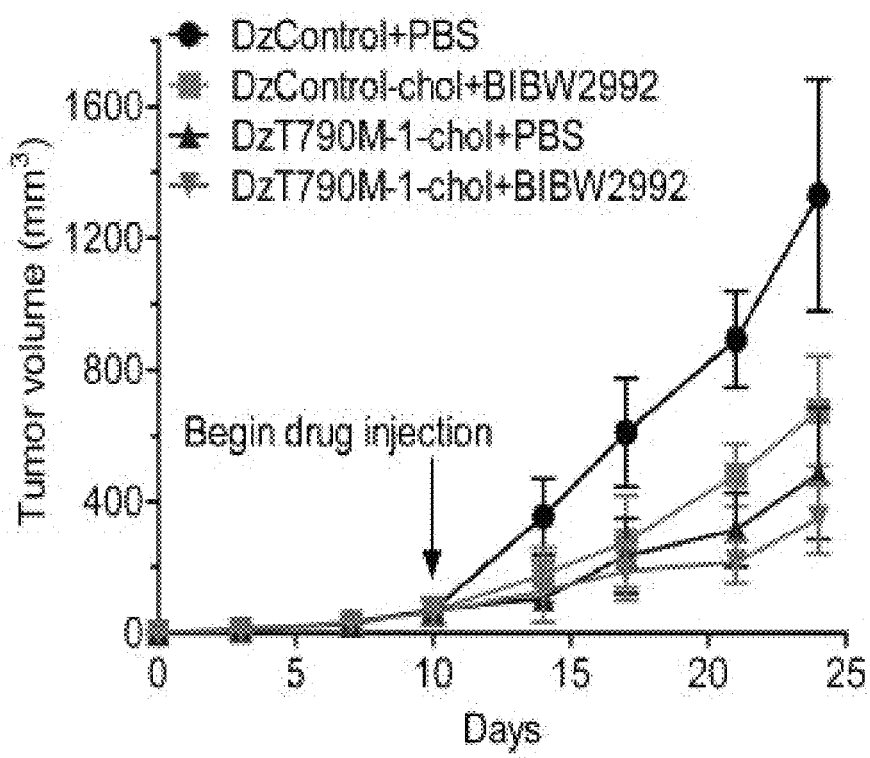
Figure 7:
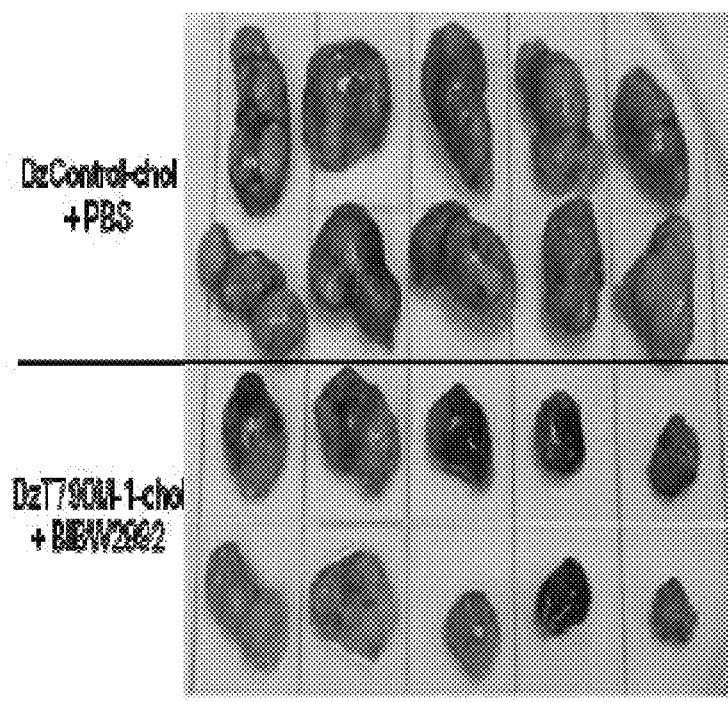

The cholesterol-modified DzT790M-1 can be used as single agents or further in combination with other clinical drugs such as EGFR TKIs or EGFR-specific antibodies. In this invention, the efficacy of combined treatment of cholesterol-modified DzT790M-1 and afatinib (BIBW2992) against T790M-derived drug resistance was evaluated both in in vitro and in vivo assays. While cholesterol-modified DzT790M significantly silenced the expression of total EGFR, pEGFR (Y1068), and pSTAT3 (Y705), the level of pAKT (S473) and pERK (T202/Y204) was slightly suppressed. On the other hand, BIBW2992 dramatically inhibited the expression of pEGFR, pAKT, and pERK when the total level of EGFR and pSTAT3 were not affected. Combined treatment of cholesterol-modified DzT790M with BIBW2992 resulted in an additive inhibition effect on EGFR expression and downstream STAT3, AKT, and ERK signaling (FIG. 7A). Furthermore, combined administration of BIBW2992 with cholesterol-modified DzT790M triggered cell death in T790M-harboring cells in a dose-dependent manner when the cell viability of EGFR wild-type cells was slightly affected (FIG. 7B). Moreover, the feasibility of combination therapy was evaluated in xenograft animal model. Compared to the control group, the tumor growth rate was inhibited at different level in all three drug-treated groups. The combined treatment group showed the highest potency in suppressing xenografted tumor growth (FIG. 7C). In summary, combined treatment of cholesterol-modified DzT790M with BIBW2992 significantly suppressed EGFR signaling and T790M-harboring cancer cell viability in vitro and inhibited tumor growth in vivo.

Example 8 Allele-Specific DNAzyme Against E746-A750 Deletion or L858R Mutation DNAzyme Against E746-A750 Deletion The DNAzyme: DzEGFR_$_\Delta$E746-A750

(GGAGATGTGTCAGCTGACTCGAATGATAGCGAC;
SEQ ID NO: 8)

was designed based on the following mRNA sequence of EGFR E746-A750 deletion.

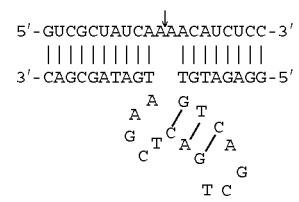

DNAzyme Against L858R Mutation

Seven DNAzymes were designed based on mRNA sequence of EGFR L858R mutant.

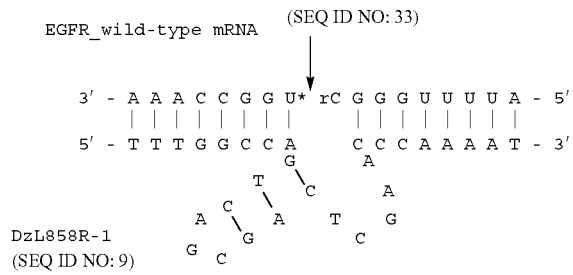
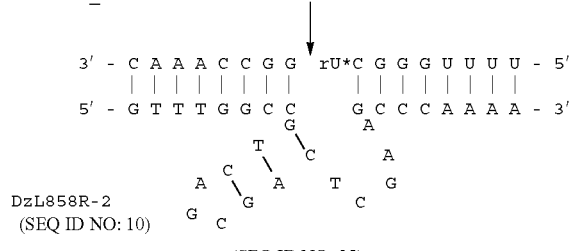
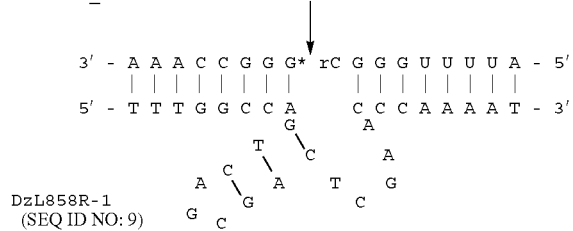
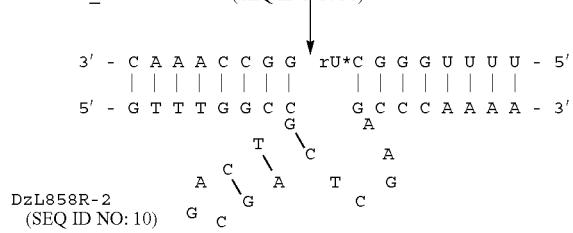
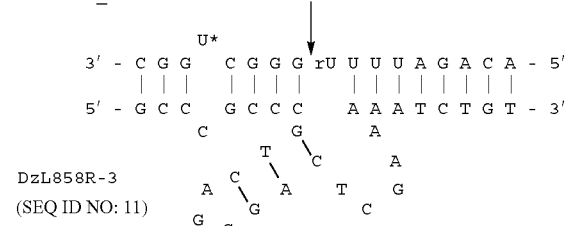
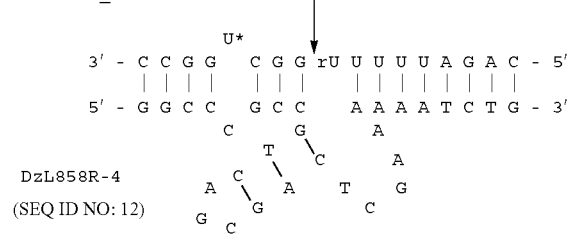
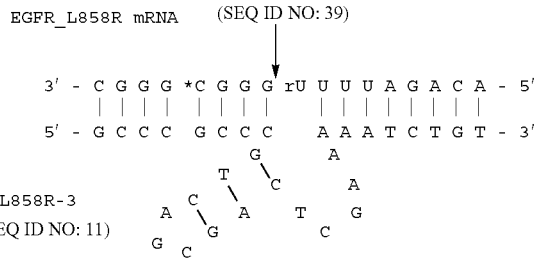
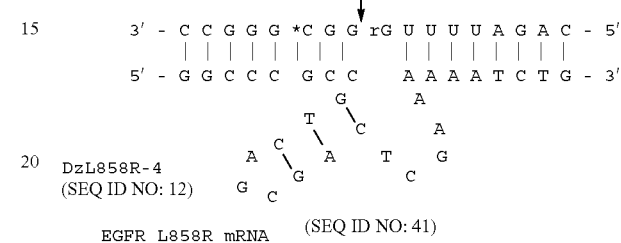
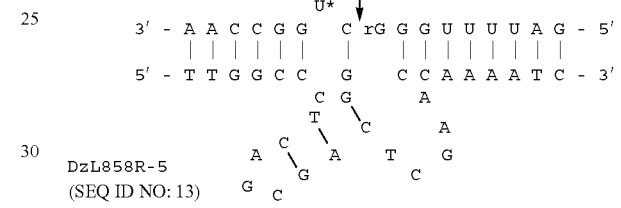
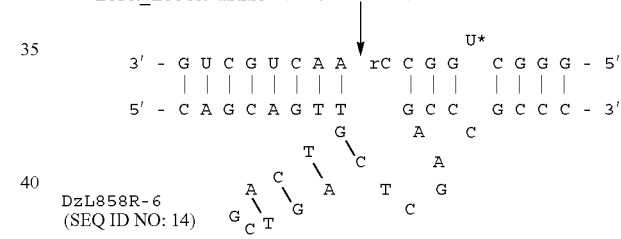
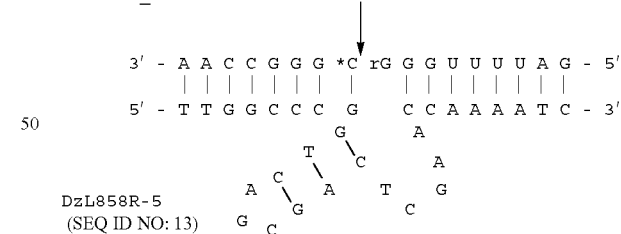
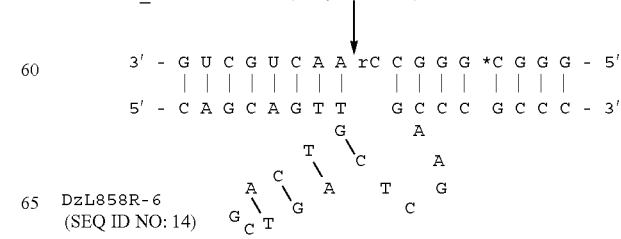

-continued

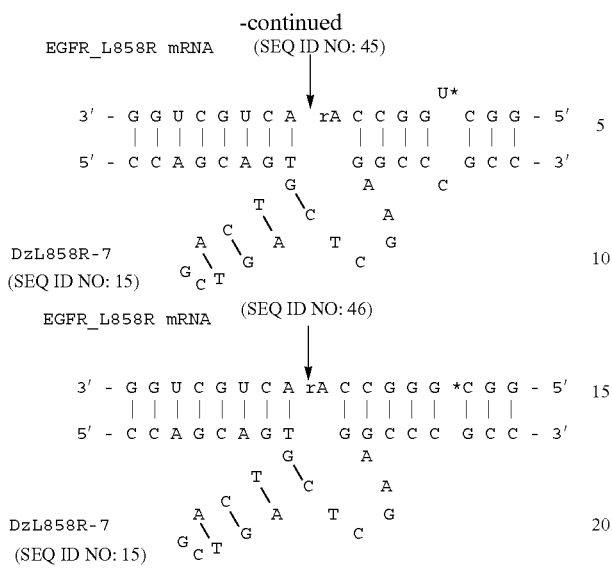

The DNAzyme sequences are listed in the following.

```
DzL858R-1:
                                    (SEQ ID NO: 9)
TTTGGCCAGTCAGCGACTCGAACCCAAAAT;

DzL858R-2:
                                    (SEQ ID NO: 10)
GTTTGGCCGTCAGCGACTCGAAGCCCAAAA;

DzL858R-3:
                                    (SEQ ID NO: 11)
GCCCGCCCGTCAGCGACTCGAAAAATCTGT;

DzL858R-4:
                                    (SEQ ID NO: 12)
GGCCCGCCGTCAGCGACTCGAAAAAATCTG;

DzL858R-5:
                                    (SEQ ID NO: 13)
TTGGCCCGGTCAGCGACTCGAACCAAAATC;

DzL858R-6:
                                    (SEQ ID NO: 14)
CAGCAGTTGTCAGCTGACTCGAAGCCCGCCC;

DzL858R-7:
                                    (SEQ ID NO: 15)
CCAGCAGTGTCAGCTGACTCGAAGGCCCGCC.
```

A549, PC9, and H1975 cells were seeded in 12-well plates at 1×10⁵ cells/well and cultured overnight. Then, A549 and PC9 cells were separately treated with 50, 100, or 150 nM control DNAzyme or DzEGFR_$_{\Delta E746\text{-}A750}$ with Lipofectamine 2000 for 48 h. A549 and H1975 cells were separately treated with 100 nM control DNAzyme or different DzL858Rs with Lipofectamine 2000 for 48 h. RNA purification was done by conventional TRIzol® (Invitrogen Corp., Grand Island, N.Y.) method following manufacturer's protocol. Quantitative RT-PCR was performed on 40 ng total mRNA with the LightCycler 480 system (Roche). The PCR mix contained 5 µl of 2× ProbeMaster mix, 100 nM of UPL probe (Roche Diagnostics, Penzberg, Germany) and 200 nM of primer (each) in a total volume of 10 µl. The PCR conditions were 95° C. for 10 min, followed by 60 cycles at 95° C. for 10 s, 60° C. for 10 s, and 72° C. for 2 s. Data were analyzed by LC480 software (Roche Diagnostics). The relative amount of EGFR mRNA was normalized to ACTB mRNA. The sequences of PCR primers are as follows:

```
EGFR:
forward primer:
                                    (SEQ ID NO: 24)
ACATCTCCGAAAGCCAACAA;

reverse primer:
                                    (SEQ ID NO: 25)
CTGCGTGATGAGCTGCAC ACTB:
forward primer:
                                    (SEQ ID NO: 26)
ATTGGCAATGAGCGGTTC;

reverse primer:
                                    (SEQ ID nO: 27)
GGATGCCACAGGACTCCAT
```

A549 and PC9 cells were seeded in 12-well plates at 1×10⁵ cells/well and cultured overnight. Then, cells were separately treated with 50, 100, or 150 nM control DNAzyme or DzEGFR_$_{\Delta E746\text{-}A750}$ with Lipofectamine 2000 for 48 h. Cells were rinsed with PBS buffer for three times and 50 µl MTT solution (0.5 mg/ml) was added. After incubation at 37° C. for 3 h, MTT solution was replaced with DMSO. The cell proliferation was measured by the absorbance at 570 nm with a microplate reader.

Figure 8:
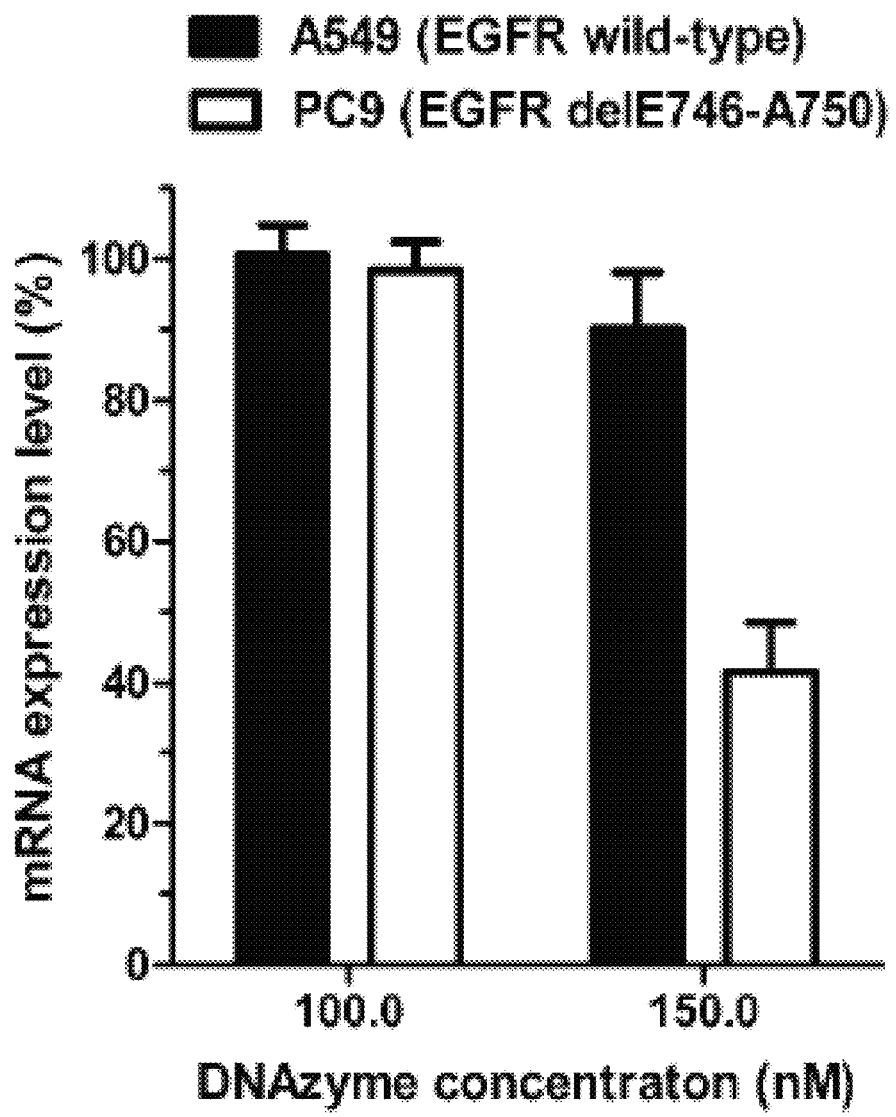
FIG. 8 shows that allele-specific DNAzyme against EGFR E746-A750 deletion mutation induces cell apoptosis in EGFR E746-A750 deletion-harboring cells.
Figure 8:
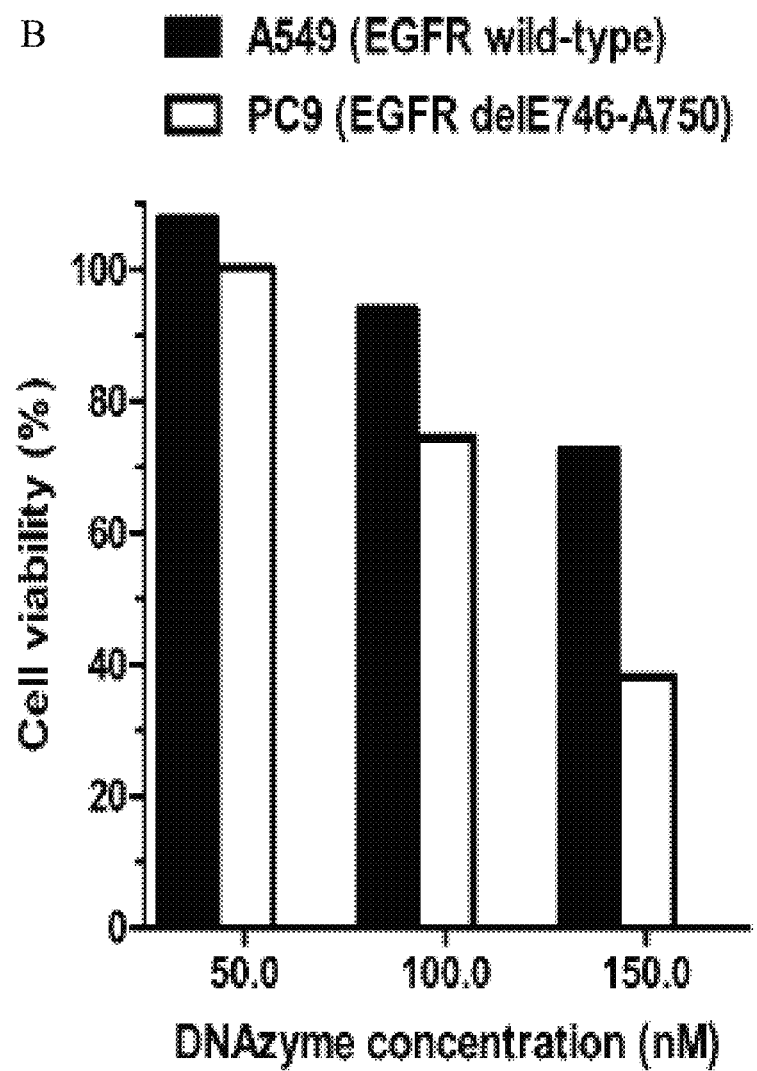

Two cell lines were used in the experiment, A549 (wild type EGFR) and PC9 (E746-A750 deletion EGFR). The EGFR mRNA extracted from both A549 and PC9 cells were sequenced and the results were in accordance with literature reports. DzEGFR_$_{\Delta E746\text{-}A750}$ with its side arm sequences complementary to the ΔE746-A750 sequence did not bind and act on the wild type EGFR. On the other hand, the mutant EGFR expression was suppressed by DzEGFR_$_{\Delta E746\text{-}A750}$ and resulted in 60% death of PC9 cells while using DzControl-treated group as 100% expression of mRNA and 0% death of PC9 cells (FIG. 8A). The viability of A549 cells was affected a bit (20%) at 150 nM of DNAzyme (FIG. 8B). The DNAzyme was transfected with high concentration of Lipofectamine 2000 which may pose toxicity to the cells. However, this could be overcome by changing delivery system or modifying DNAzyme structure.

Figure 9:
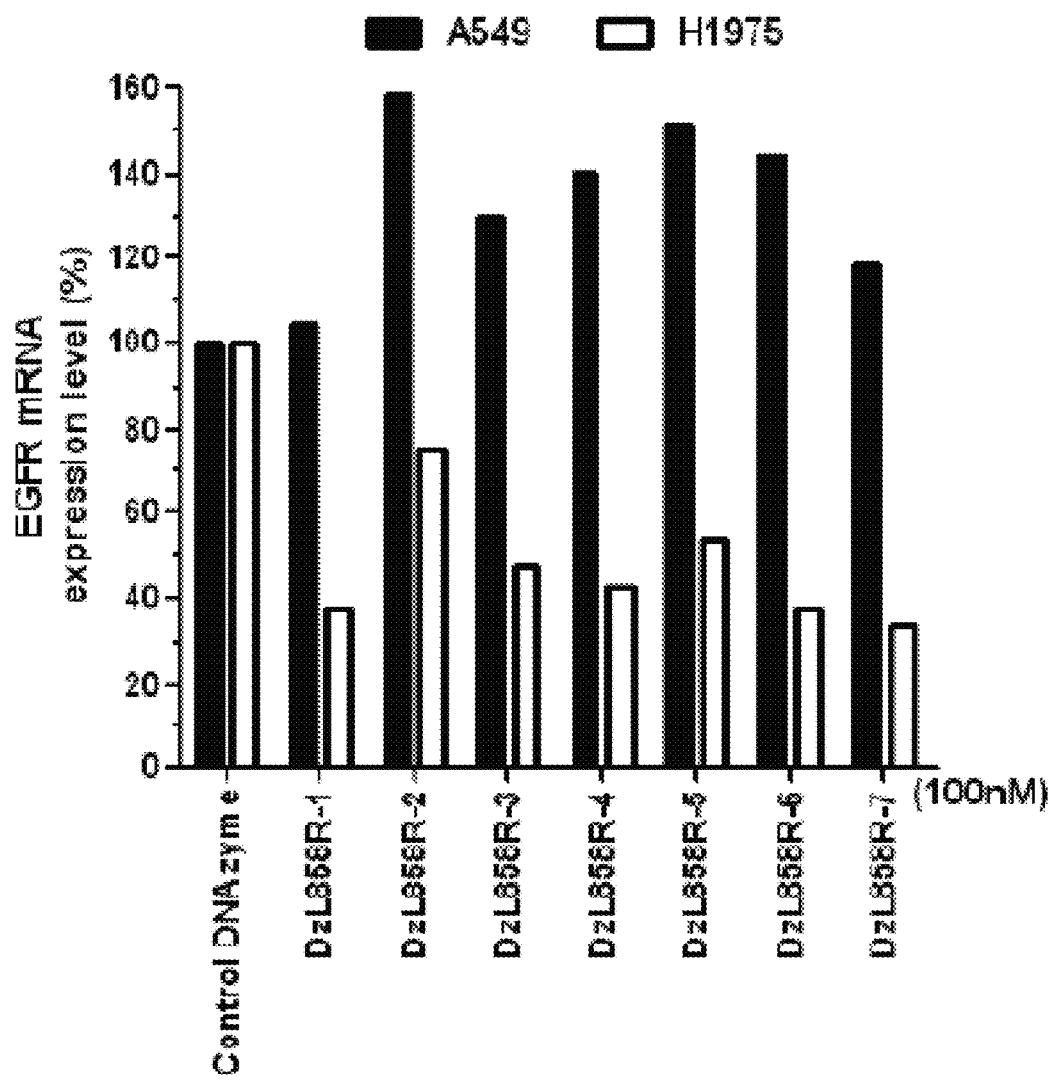
FIG. 9 shows that allele-specific DNAzyme against EGFR L858R mutation induces cell apoptosis in EGFR L858R-harboring cells.

As shown in FIG. 9, L858R DNAzymes selectively and significantly silencing EGFR mRNA expression of H1975 cell line, which harbors EGFR L858R mutant. On the contrary, L858R DNAzyme showed little effect on the mRNA expression of EGFR in A549 cell line (wild-type EGFR).

Example 9 DzT or cDzT Treatment Suppresses EGF-Mediated Signaling in T790M-Mutant Cell Lines H1975$^{TM/LR}$ and CL97$^{TM/GA}$ cells were harvested 72 h after transfecting with DzC or DzT. Potential EGF-mediated signaling was activated by adding 100 ng/ml EGF 15 min before cell lysates were harvested.

Figure 10:
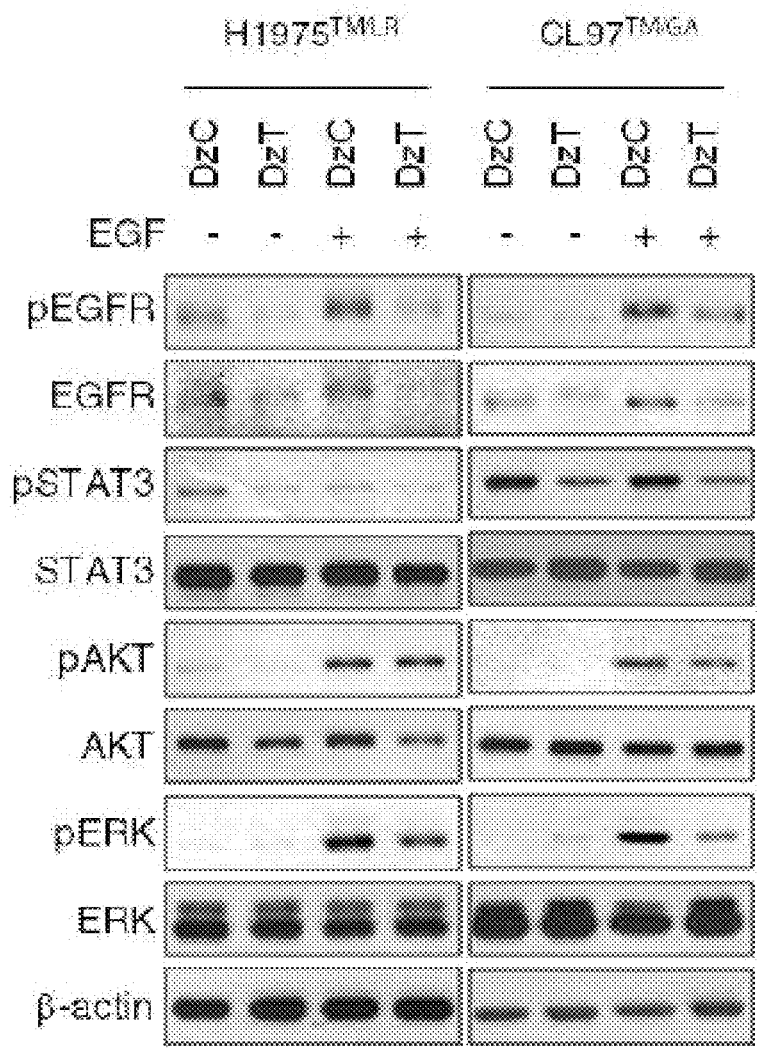
FIG. 10 shows that DzT remains its suppression effect on EGFR T790M expression and downstream signaling after EGF treatment in T790M mutant cells. Cells were harvested 72 h after transfecting with 100 nM DzC or DzT. 100 ng/ml EGF were added into culture medium 15 min before cell lysates were harvested. Cell lysates were analyzed by immunoblotting with indicated primary antibodies.
Figure 11:
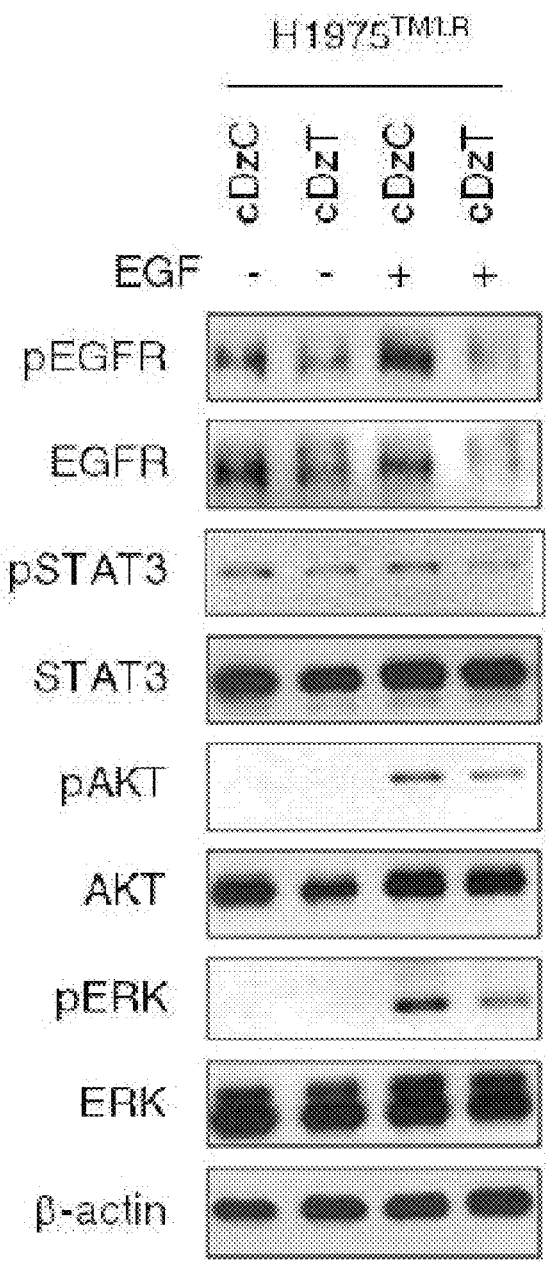
FIG. 11 shows that cDzT remains its suppression effect on EGFR T790M expression and downstream signaling after EGF treatment in H1975$^{TM/LR}$. Cells were harvested 72 h after transfecting with 100 nM cDzC or cDzT. 100 ng/ml EGF were added into culture medium 15 min before cell lysates were harvested. Cell lysates were analyzed by immunoblotting with indicated primary antibodies.

After EGF treatment, both DzC and DzT treated group revealed elevated phosphorylation level of EGFR, AKT, and ERK in H1975$^{TM/LR}$ compared to two groups without EGF treatment (FIG. 10, left panel). This data indicates a successful activation of EGF-mediated signaling in H1975$^{TM/LR}$. Under this condition, DzT remained its suppression effect on EGFR protein expression and downstream signaling including EGFR, STAT3, and ERK but not AKT. Similar results were detected in CL97$^{TM/GA}$ cell line (FIG. 10, right panel). In cDzT treated H1975$^{TM/LR}$ cells, cDzT treatment inhibited EGFR protein expression and downstream signaling including EGFR, STAT3, AKT, and ERK after EGF treatment (FIG. 11).

Example 10 DzT or cDzT Treatment Suppresses EGF-Mediated Signaling in T790M-Mutant Cell Lines H1975 and CL97 cells were treated with 25, 50 nM cDzC or cDzT together with 25, 50, 75, 100, 150, 250 nM BIBW-2992 or DMSO (vehicle control) added to the culture medium. Seventy-two hours after treatment, MTT assays were performed to monitor cell viability. Combination index (CI) values were calculated using CompuSyn version 3.0.1 software (ComboSyn, Inc., Paramus, N.J., USA) by CI equation of Chou-Talalay.

$$CI = \frac{(D)_1}{(D_x)_1} + \frac{(D)_2}{(D_x)_2}$$

$(D_x)_1$ is the dose of cDzT alone that inhibits x % of cell viability while $(D_x)_2$ is the dose of BIBW-2992 alone that inhibits x % of cell viability. $(D)_1$ is the portion of cDzT and $(D)_2$ is the portion of BIBW-2992 that achieve x % of inhibition when combined treatment of cDzT and BIBW-2992. "Fraction affected (Fa)" on the x-axis of Fa-CI plot represented the fraction of cell viability inhibition on drug treated cells. CI values greater than 1, equal to 1, and less than 1 indicate antagonistic effects, additive effects, and synergistic effects, respectively.

Figure 12:
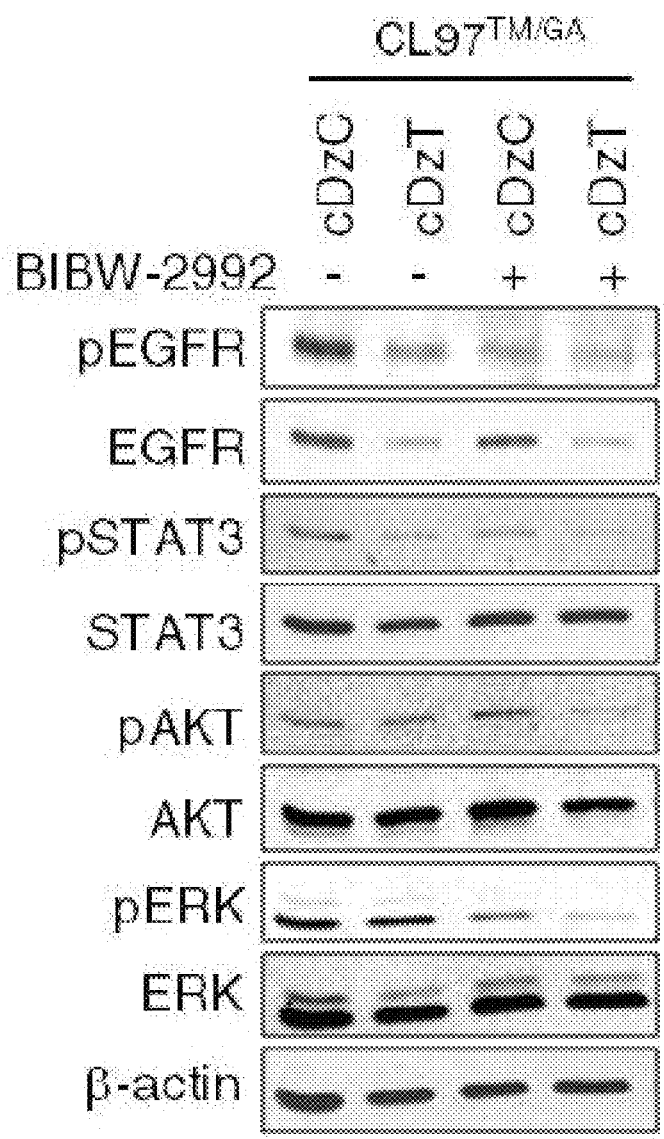
FIG. 12 shows that combined treatment of cDzT and BIBW-2992 significantly suppresses the phosphorylation of STAT3, AKT, and ERK in CL97TM/GA cells Immunoblot analysis of CL97TM/GA cells treated with cDzC or cDzT (50 nM) incubated with or without added BIBW-2992 (200 nM).

At suboptimal concentrations, individual drugs did not efficiently suppress downstream signaling (FIG. 12). At this concentration, cDzT alone mainly inhibited EGFR phosphorylation, EGFR expression, and STAT3 signaling in $CL97^{TM/GA}$. BIBW-2992 alone suppressed the phosphorylation level of EGFR in $CL97^{TM/GA}$ cells. ERK signaling was suppressed in $CL97^{TM/GA}$. In contrast, combined treatment significantly suppressed all of the downstream effectors including the phosphorylation of STAT3, AKT, and ERK.

Figure 13:
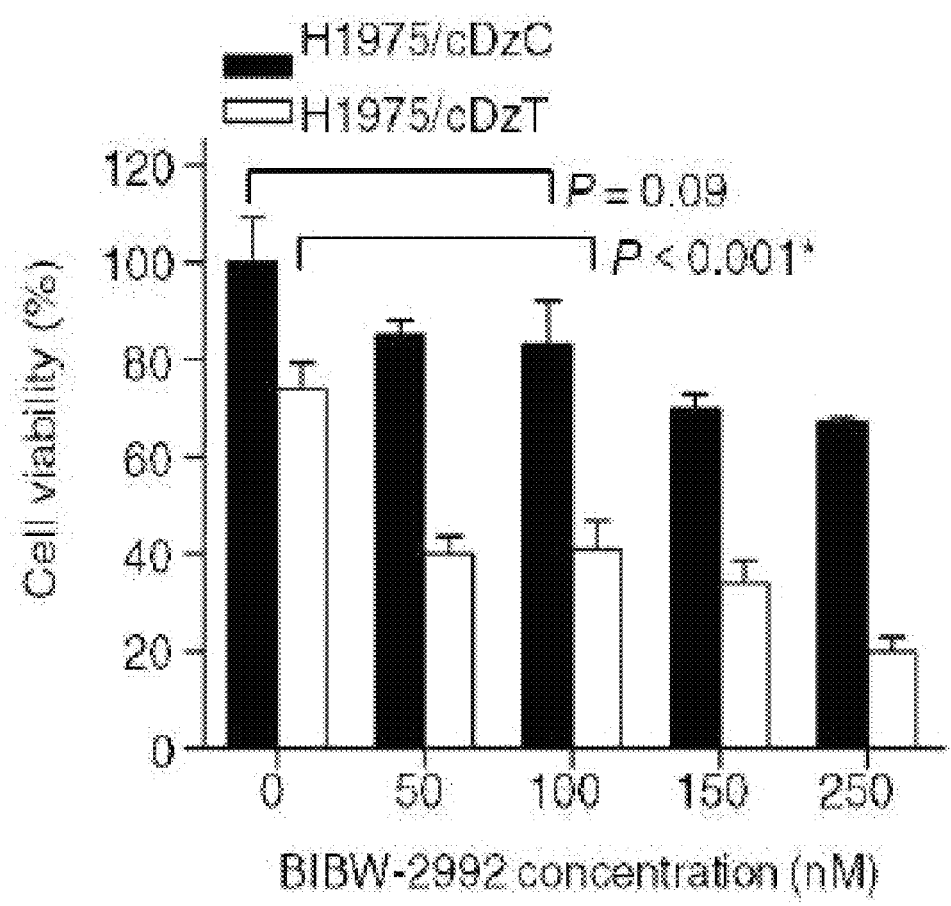
FIG. 13 shows that combined treatment of cDzT and BIBW-2992 exerts a synergistic inhibitory effect on cell viability in cells harboring EGFR T790M mutants. MTT assay of H1975$^{TM/LR}$ cells (a, b) or CL97$^{TM/GA}$ cells (c, d) treated with cDzC or cDzT (25 nM) combined with 25 nM (●), 50 nM (■), 75 nM (★), 100 nM (▲), 150 nM (▼), or 250 nM (♦) BIBW-2992 (n=3). The data are presented as the means±SD. The results were analyzed by Student's t-test and CI calculation. An asterisk denotes statistical significant difference.
Figure 13:
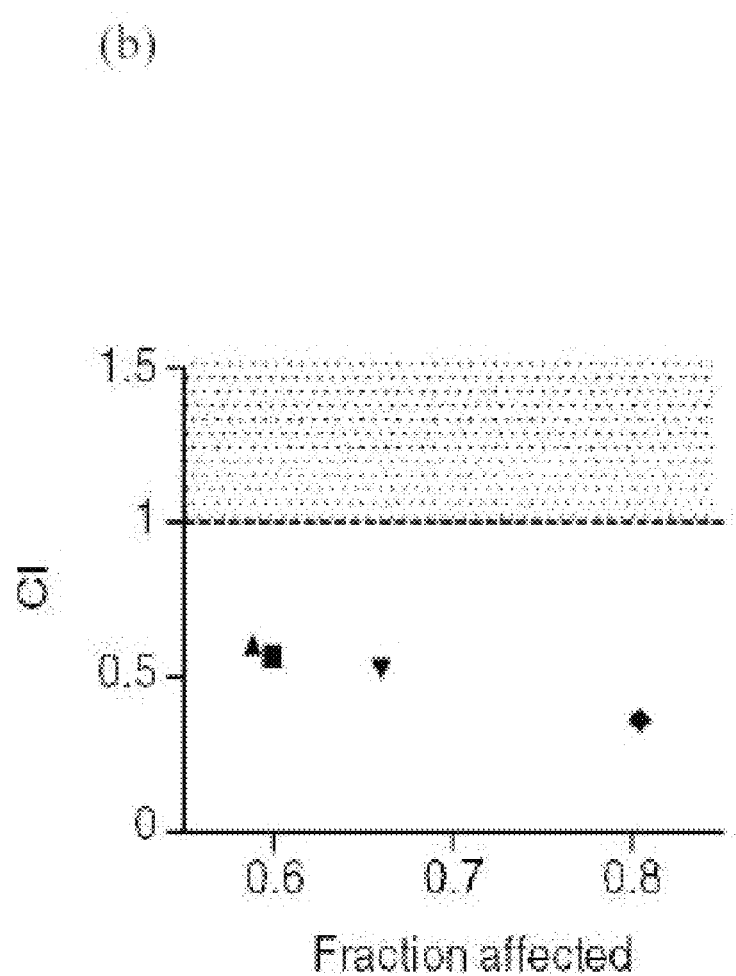
Figure 13:
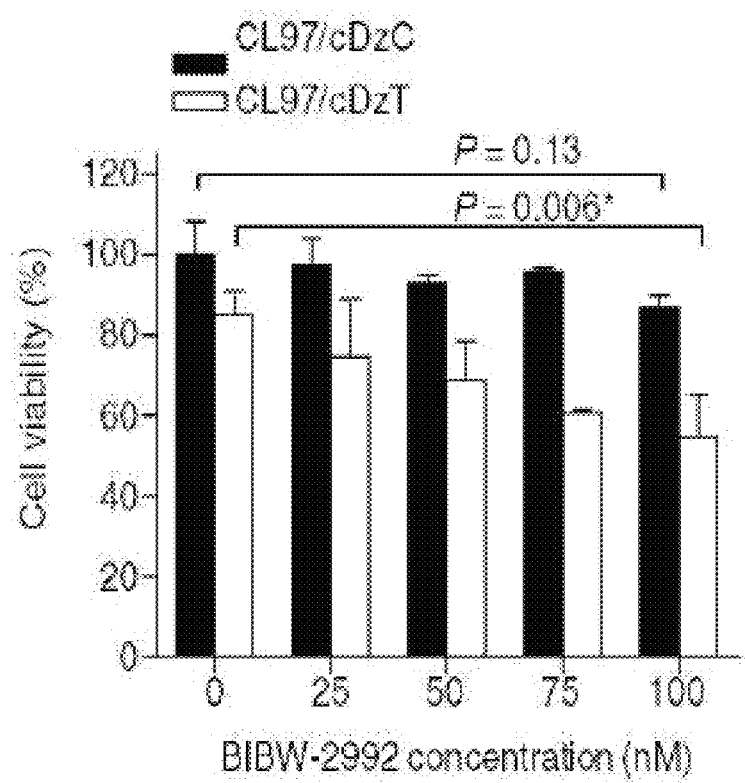
Figure 13:
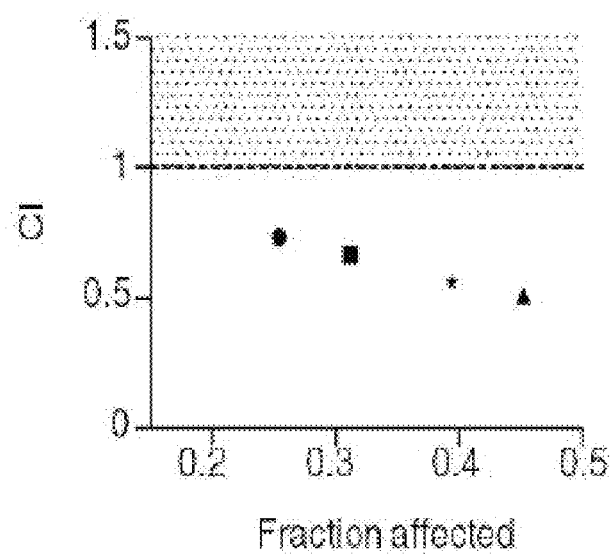

The results showed that BIBW-2992 enhanced the cell-killing effect of cDzT in both $H1975^{TM/LR}$ and $CL97^{TM/GA}$ cells in a concentration-dependent manner (FIGS. 13a and 13c). The CI value was around 0.4 to 0.6 in $H1975^{TM/LR}$ (FIG. 13b) while the CI value was around 0.5 to 0.7 in $CL97^{TM/GA}$ (FIG. 13d). These data suggested that the combined treatment of cDzT and BIBW-2992 exerted a synergistic inhibitory effect on cell viability in cells harboring EGFR T790M mutants.

Example 11 Synergistic Anti-Tumor Effect of Combined Treatment with cDzT and BIBW-2992 In Vivo All animal studies were performed according to protocols approved by the Laboratory Animal Center, Academia Sinica. Eight-week old Balb/c nude mice (BioLASCO, Taipei, Taiwan) were subcutaneously inoculated with $2 \times 10^6$ $H1975^{TM/LR}$ cells (day 0). In the combined-treatment study, mice were randomly divided into four groups on day 10 and administered the following drug or drug combinations: (1) cDzC, (2) cDzC+BIBW-2992, (3) cDzT, or (4) cDzT+BIBW-2992. Chol-TEG-modified DNAzyme (500 pmoles) mixed with Lipofectamine 2000 was injected intratumorally twice per week. BIBW-2992 was suspended in PBS and administered three times per week by oral gavage at 20 mg/kg. The length (L) and width (W) of tumors were measured with calipers every 3-4 days, and tumor volumes were calculated as $(L \times W^2)/2$. After mice were sacrificed, tumors were excised. Small sections of tumors were processed for immunoblot and the remaining tumor tissue was fixed with 10% formalin and embedded in paraffin. Xenograft tumor slides were stained with hematoxylin and eosin (H&E), anti-EGFR (L858R mutant specific; Cell Signaling), and anti-caspase 3 (Cell Signaling).

Figure 14:
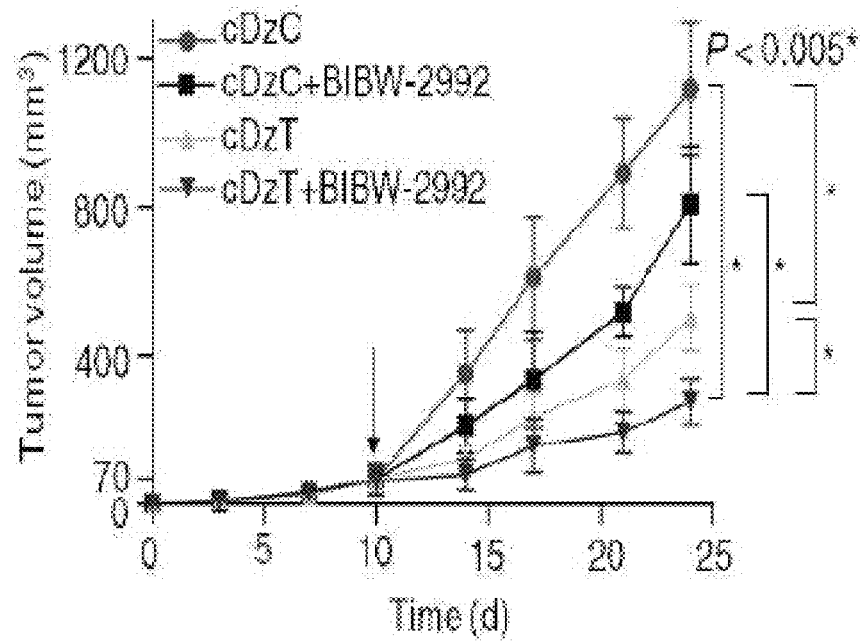
FIG. 14 shows that synergistic effects of cDzT and BIBW-2992. (a-c) Combined treatment silences EGFR signaling, triggers apoptosis, and suppresses xenograft tumor growth. (a) cDzT (500 pmoles) was intratumorally injected (twice per week) and BIBW-2992 (20 mg/kg) was orally administered (three times per week) 10 days (arrow indicated) after inoculating xenograft mice with H1975$^{TM/LR}$ (n=7). The data are presented as means±SD and were analyzed by Student's t-test. Asterisks denote statistical significant differences (P<0.005). (b) Xenograft tumor tissues were processed for immunostaining. Scale bars represent 200·m in H&E images and 100·m in EGFR L858R and caspase-3 images. (c) Xenograft tumor tissues were processed for immunoblotting.
Figure 14:
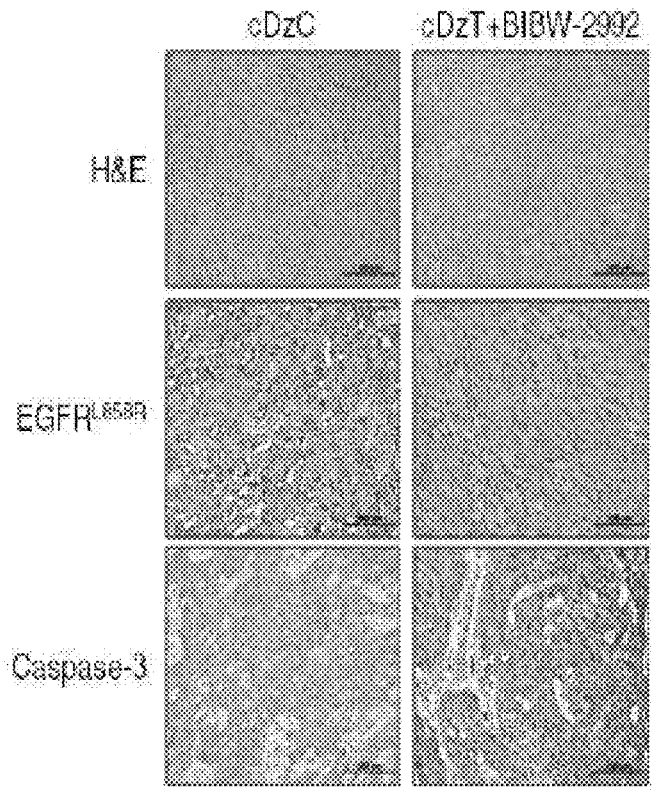
Figure 14:
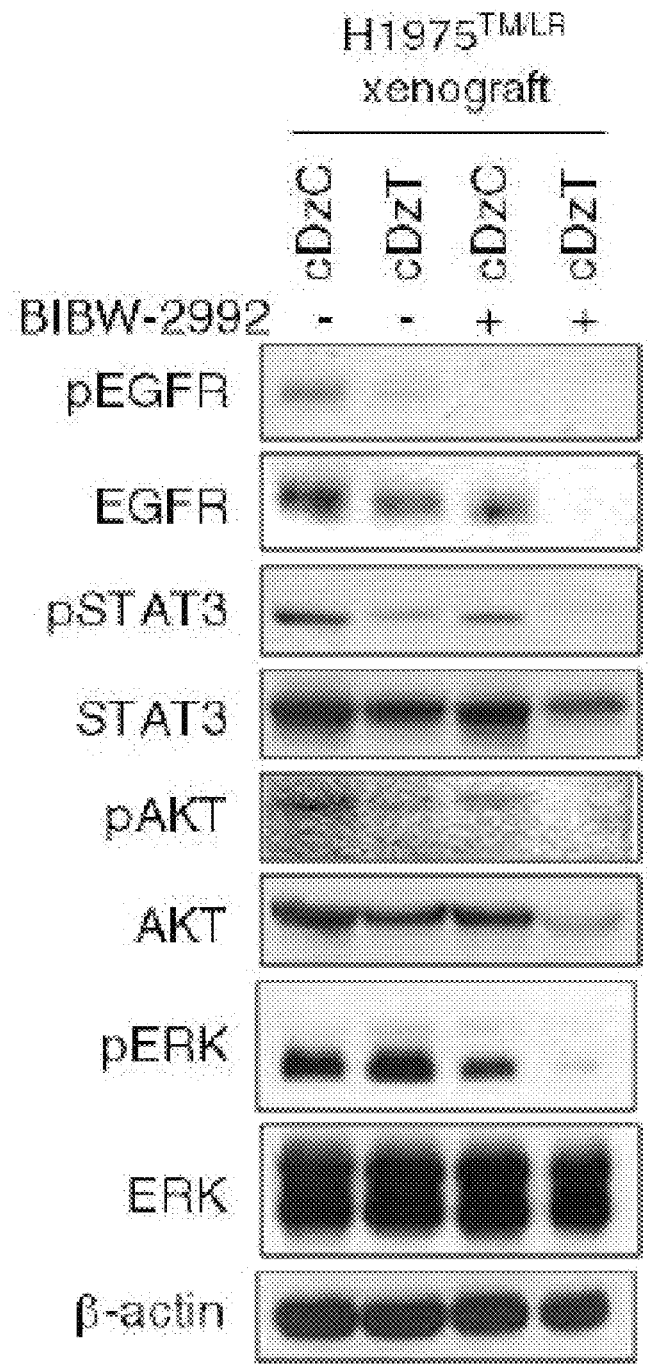

Synergistic effects of cDzT and BIBW-2992 were also seen in the xenograft animal model. Compared with the control group (cDzC), all three drug-treated groups (cDzC+BIBW-2992, cDzT, and cDzT+BIBW-2992) inhibited the growth of tumor originated from $H1975^{TM/LR}$ cells to different degrees (FIG. 14a). Combined treatment with cDzT and BIBW-2992 showed the highest potency among all treatments in suppressing xenograft tumor growth. In this group, the average size of excised tumors was approximately 4-fold smaller than that in the control group. An immunohistochemical analysis of tumor tissues showed severe necrosis in tumor tissues from the combined treatment group but not in tissues from the control group (FIG. 14b, upper panel). EGFR in $H1975^{TM/LR}$ cells contains both L858R and T790M mutations, and thus can be detected using an antibody specific for the L858R mutant form. Tumor sections from the combined treatment group exhibited lower levels of EGFR L858R expression accompanied by higher caspase-3 protein expression levels compared with sections from the control group (FIG. 14c, middle and lower panel). Tumor tissues were also evaluated for EGFR expression and downstream signaling. The results showed that the combination of cDzT and BIBW-2992 further suppressed total EGFR expression, the phosphorylation of EGFR in tumor tissues, and the levels of the phosphorylated forms of STAT3, AKT, and ERK compared with the control group (FIG. 14d). Taken together, these results indicate that the combination of cDzT and BIBW-2992 synergistically inhibits EGFR protein expression and downstream signaling, triggering T790M-harboring cells to undergo apoptosis and suppressing xenograft tumor growth.

---

What is claimed is:

1. An oligonucleotide or a modified sequence thereof, which specifically hybridizes to EGFR mutation mRNA so as to inhibit the translation thereof in a cell, wherein the oligonucleotide comprises consecutive nucleotides having a sequence selected from the group consisting of SEQ ID NOs:1 to 7.

2. The oligonucleotide or a modified sequence thereof of claim 1, which has the sequence of SEQ ID NO:1 or SEQ ID NO:2.

3. The oligonucleotide or a modified sequence thereof of claim 1, which has the sequence of SEQ ID NO:1.

4. The oligonucleotide or a modified sequence thereof of claim 1, wherein the modified sequence comprises a modified base on nucleotide structure, a modified linkage bond between nucleotides, or a functional group at the 5'- or 3'-end of the oligonucleotide.

5. The oligonucleotide or a modified sequence thereof of claim 4, wherein the modified base is amine-modified dA, phenol-modified dU, imidazole-modified dU, or pyridine-modified U.

6. The oligonucleotide or a modified sequence thereof of claim 1, wherein the modified sequence comprises a phosphorothioate bond between 3 bases at both ends and a cholesterol-TEG group at the 3'-end.

7. A vector which comprises a sequence encoding the oligonucleotide or a modified sequence thereof of any of claims 1 and 2-6.

8. A host which comprises the vector of claim 7.

9. A pharmaceutical composition comprising the oligonucleotide or a modified sequence thereof of any of claim 1 and a pharmaceutically acceptable carrier.

10. The pharmaceutical composition of claim 9, which further comprises an EGFR TK inhibitor or an EGFR-specific antibody.

11. The pharmaceutical composition of claim 10, wherein the EGFR TK inhibitor is afatinib (BIBW2992), XL647 (N-(3,4-dichloro-2-fluorophenyl)-6-methoxy-7-(((3aR,6aS)-2-methyloctahydrocyclopenta[c]pyrrol-5-yl)methoxy)quinazolin-4-amine), Neratinib (HKI-272), dacomitinib (PF-00299804), BMS-6690514 ((3R,4R)-4-Amino-1-[[4-[(3-methoxyphenyl)amino]pyrrolo[2,1-f][1,2,4]triazin-5-yl]methyl]piperidin-3-ol), gefitinib or erlotinib.

12. The pharmaceutical composition of claim 10, wherein the EGFR-specific antibody is cetuximab or panitumumab.

13. A method of specifically inhibiting the expression of EGFR mutation mRNA in a cell that would otherwise express EGFR mutation protein, comprising contacting the cell with either of the oligonucleotides of any of claims 1 and 2-6 so as to specifically inhibit the expression of EGFR mutation protein in the cell.

14. A method of specifically inhibiting the expression of EGFR T790M mutation mRNA in a cell that would otherwise express EGFR T790M Protein, comprising contacting the cell with either of the oligonucleotides or a modified sequence thereof of any of claims 1 and 2-6 so as to specifically inhibit the expression of EGFR T790M protein in the cell.

15. A method of treating an EGFR-dependent cancer in a subject, comprising administering an effective amount of an oligonucleotide or a modified sequence thereof of any of claims 1 and 2-6 to the subject.

16. The method of claim 15, which can be used as an adjuvant therapy given after surgery, radiation or chemotherapy.

17. A method of treating EGFR-dependent cancer in a subject, comprising administering a TKI inhibitor or an EGFR-specific antibody and an oligonucleotide or a modified sequence thereof of any of claims 1 and 2-6 to the subject.

18. The method of claim 17, wherein the TKI inhibitor or a EGFR-specific antibody and an oligonucleotide or a modified sequence thereof of any of claims 1 and 2-6 can be administered concurrently, sequentially or separately.

19. The method of claim 17, wherein the EGFR TK inhibitor is afatinib (BIBW2992), XL647 (N-(3,4-dichloro-2-fluorophenyl)-6-methoxy-7-(((3aR,6aS)-2-methyloctahydrocyclopenta[c]pyrrol-5-yl)methoxy)quinazolin-4-amine), Neratinib (HKI-272), dacomitinib (PF-00299804), BMS-6690514 ((3R,4R)-4-Amino-1-[[4-[(3-methoxyphenyl)amino]pyrrolo[2,1-f][1,2,4]triazin-5-yl]methyl]piperidin-3-ol), gefitinib or erlotinib.

20. The method of claim 17, wherein the EGFR-specific antibody is cetuximab or panitumumab.

21. The method of claim 15, wherein the EGFR-dependent cancer is a lung cancer.

22. The method of claim 21, wherein the lung cancer is NSCLC.

23. The method of claim 17, wherein the EGFR-dependent cancer is a lung cancer.

24. The method of claim 23, wherein the lung cancer is NSCLC.

* * * * *

SEQUENCE LISTING

```
<160> NUMBER OF SEQ ID NOS: 47

<210> SEQ ID NO 1
<211> LENGTH: 29
<212> TYPE: DNA
<213> ORGANISM: Artificial Sequence
<220> FEATURE:
<223> OTHER INFORMATION: an oligonucleotide or a modified sequence
      thereof specifically hybridizes to EGFR T790M mRNA so as to
      inhibit the translation thereof in a cell
```

```
<400> SEQUENCE: 1
agctgcatga ggctagctac aacgagagc                                      29

<210> SEQ ID NO 2
<211> LENGTH: 31
<212> TYPE: DNA
<213> ORGANISM: Artificial Sequence
<220> FEATURE:
<223> OTHER INFORMATION: an oligonucleotide or a modified sequence
      thereof specifically hybridizes to EGFR T790M mRNA so as to
      inhibit the translation thereof in a cell

<400> SEQUENCE: 2
gagctgcagg ctagctacaa cgagatgagc t                                   31

<210> SEQ ID NO 3
<211> LENGTH: 30
<212> TYPE: DNA
<213> ORGANISM: Artificial Sequence
<220> FEATURE:
<223> OTHER INFORMATION: an oligonucleotide or a modified sequence
      thereof specifically hybridizes to EGFR T790M mRNA so as to
      inhibit the translation thereof in a cell

<400> SEQUENCE: 3
catgaggcta gctacaacga gagctgcacg                                     30

<210> SEQ ID NO 4
<211> LENGTH: 31
<212> TYPE: DNA
<213> ORGANISM: Artificial Sequence
<220> FEATURE:
<223> OTHER INFORMATION: an oligonucleotide or a modified sequence
      thereof specifically hybridizes to EGFR T790M mRNA so as to
      inhibit the translation thereof in a cell

<400> SEQUENCE: 4
ctgcatgagg ctagctacaa cgagagctgc a                                   31

<210> SEQ ID NO 5
<211> LENGTH: 31
<212> TYPE: DNA
<213> ORGANISM: Artificial Sequence
<220> FEATURE:
<223> OTHER INFORMATION: an oligonucleotide or a modified sequence
      thereof specifically hybridizes to EGFR T790M mRNA so as to
      inhibit the translation thereof in a cell

<400> SEQUENCE: 5
ggcatgagtg tcagcgactc gaagcatgat g                                   31

<210> SEQ ID NO 6
<211> LENGTH: 29
<212> TYPE: DNA
<213> ORGANISM: Artificial Sequence
<220> FEATURE:
<223> OTHER INFORMATION: an oligonucleotide or a modified sequence
      thereof specifically hybridizes to EGFR T790M mRNA so as to
      inhibit the translation thereof in a cell

<400> SEQUENCE: 6
agggcatgag tgtcagcgac tcgaagcat                                      29

<210> SEQ ID NO 7
<211> LENGTH: 29
<212> TYPE: DNA
<213> ORGANISM: Artificial Sequence
```

```
<220> FEATURE:
<223> OTHER INFORMATION: an oligonucleotide or a modified sequence
      thereof specifically hybridizes to EGFR T790M mRNA so as to
      inhibit the translation thereof in a cell

<400> SEQUENCE: 7
tgagtgtcag cgactcgaag catgatgag                                        29

<210> SEQ ID NO 8
<211> LENGTH: 33
<212> TYPE: DNA
<213> ORGANISM: Artificial Sequence
<220> FEATURE:
<223> OTHER INFORMATION: an oligonucleotide or a modified sequence
      thereof specifically hybridizes to EGFR E746-A750 deletion mRNA so
      as to inhibit the translation thereof in a cell

<400> SEQUENCE: 8
ggagatgtgt cagctgactc gaatgatagc gac                                   33

<210> SEQ ID NO 9
<211> LENGTH: 30
<212> TYPE: DNA
<213> ORGANISM: Artificial Sequence
<220> FEATURE:
<223> OTHER INFORMATION: an oligonucleotide or a modified sequence
      thereof specifically hybridizes to EGFR L858R mRNA so as to
      inhibit the translation thereof in a cell

<400> SEQUENCE: 9
tttggccagt cagcgactcg aacccaaaat                                       30

<210> SEQ ID NO 10
<211> LENGTH: 30
<212> TYPE: DNA
<213> ORGANISM: Artificial Sequence
<220> FEATURE:
<223> OTHER INFORMATION: an oligonucleotide or a modified sequence
      thereof specifically hybridizes to EGFR L858R mRNA so as to
      inhibit the translation thereof in a cell

<400> SEQUENCE: 10
gtttggccgt cagcgactcg aagcccaaaa                                       30

<210> SEQ ID NO 11
<211> LENGTH: 30
<212> TYPE: DNA
<213> ORGANISM: Artificial Sequence
<220> FEATURE:
<223> OTHER INFORMATION: an oligonucleotide or a modified sequence
      thereof specifically hybridizes to EGFR L858R mRNA so as to
      inhibit the translation thereof in a cell

<400> SEQUENCE: 11
gcccgcccgt cagcgactcg aaaaatctgt                                       30

<210> SEQ ID NO 12
<211> LENGTH: 30
<212> TYPE: DNA
<213> ORGANISM: Artificial Sequence
<220> FEATURE:
<223> OTHER INFORMATION: an oligonucleotide or a modified sequence
      thereof specifically hybridizes to EGFR L858R mRNA so as to
      inhibit the translation thereof in a cell

<400> SEQUENCE: 12
ggcccgccgt cagcgactcg aaaaaatctg                                       30
```

```
<210> SEQ ID NO 13
<211> LENGTH: 30
<212> TYPE: DNA
<213> ORGANISM: Artificial Sequence
<220> FEATURE:
<223> OTHER INFORMATION: an oligonucleotide or a modified sequence
      thereof specifically hybridizes to EGFR L858R mRNA so as to
      inhibit the translation thereof in a cell

<400> SEQUENCE: 13
ttggcccggt cagcgactcg aaccaaaatc                                     30

<210> SEQ ID NO 14
<211> LENGTH: 31
<212> TYPE: DNA
<213> ORGANISM: Artificial Sequence
<220> FEATURE:
<223> OTHER INFORMATION: an oligonucleotide or a modified sequence
      thereof specifically hybridizes to EGFR L858R mRNA so as to
      inhibit the translation thereof in a cell

<400> SEQUENCE: 14
cagcagttgt cagctgactc gaagcccgcc c                                   31

<210> SEQ ID NO 15
<211> LENGTH: 31
<212> TYPE: DNA
<213> ORGANISM: Artificial Sequence
<220> FEATURE:
<223> OTHER INFORMATION: an oligonucleotide or a modified sequence
      thereof specifically hybridizes to EGFR L858R mRNA so as to
      inhibit the translation thereof in a cell

<400> SEQUENCE: 15
ccagcagtgt cagctgactc gaaggcccgc c                                   31

<210> SEQ ID NO 16
<211> LENGTH: 15
<212> TYPE: DNA
<213> ORGANISM: Artificial Sequence
<220> FEATURE:
<223> OTHER INFORMATION: the catalytic domain of the catalytic
      deoxyribonucleic acid molecule for 10-23 catalytic core sequence

<400> SEQUENCE: 16
ggctagctac aacga                                                     15

<210> SEQ ID NO 17
<211> LENGTH: 14
<212> TYPE: DNA
<213> ORGANISM: Artificial Sequence
<220> FEATURE:
<223> OTHER INFORMATION: the catalytic domain of the catalytic
      deoxyribonucleic acid molecule for 8-17 catalytic core sequence

<400> SEQUENCE: 17
gtcagcgact cgaa                                                      14

<210> SEQ ID NO 18
<211> LENGTH: 15
<212> TYPE: DNA
<213> ORGANISM: Artificial Sequence
<220> FEATURE:
<223> OTHER INFORMATION: the catalytic domain of the catalytic
      deoxyribonucleic acid molecule for 8-17 catalytic core sequence

<400> SEQUENCE: 18
```
gtcagctgac tcgaa                                                    15

<210> SEQ ID NO 19
<211> LENGTH: 20
<212> TYPE: DNA
<213> ORGANISM: Artificial Sequence
<220> FEATURE:
<223> OTHER INFORMATION: the catalytic domain of the catalytic
      deoxyribonucleic acid molecule for bipartite catalytic core
      sequence

<400> SEQUENCE: 19
aggaggtagg ggttccgctc                                               20

<210> SEQ ID NO 20
<211> LENGTH: 20
<212> TYPE: DNA
<213> ORGANISM: Artificial Sequence
<220> FEATURE:
<223> OTHER INFORMATION: PCR primer for EGFR

<400> SEQUENCE: 20
acctgctcaa ctggtgtgtg                                               20

<210> SEQ ID NO 21
<211> LENGTH: 20
<212> TYPE: DNA
<213> ORGANISM: Artificial Sequence
<220> FEATURE:
<223> OTHER INFORMATION: PCR primer for EGFR

<400> SEQUENCE: 21
ccaatgccat ccacttgata                                               20

<210> SEQ ID NO 22
<211> LENGTH: 20
<212> TYPE: DNA
<213> ORGANISM: Artificial Sequence
<220> FEATURE:
<223> OTHER INFORMATION: PCR primer for ACTB

<400> SEQUENCE: 22
tcctccctgg agaagagcta                                               20

<210> SEQ ID NO 23
<211> LENGTH: 20
<212> TYPE: DNA
<213> ORGANISM: Artificial Sequence
<220> FEATURE:
<223> OTHER INFORMATION: PCR primer for ACTB

<400> SEQUENCE: 23
cgatccacac ggagtacttg                                               20

<210> SEQ ID NO 24
<211> LENGTH: 20
<212> TYPE: DNA
<213> ORGANISM: Artificial Sequence
<220> FEATURE:
<223> OTHER INFORMATION: real-time PCR primer for EGFR

<400> SEQUENCE: 24
acatctccga aagccaacaa                                               20

<210> SEQ ID NO 25
<211> LENGTH: 18

```
<212> TYPE: DNA
<213> ORGANISM: Artificial Sequence
<220> FEATURE:
<223> OTHER INFORMATION: real-time PCR primer for EGFR

<400> SEQUENCE: 25
ctgcgtgatg agctgcac                                                  18

<210> SEQ ID NO 26
<211> LENGTH: 18
<212> TYPE: DNA
<213> ORGANISM: Artificial Sequence
<220> FEATURE:
<223> OTHER INFORMATION: real-time PCR primer for ACTB

<400> SEQUENCE: 26
attggcaatg agcggttc                                                  18

<210> SEQ ID NO 27
<211> LENGTH: 19
<212> TYPE: DNA
<213> ORGANISM: Artificial Sequence
<220> FEATURE:
<223> OTHER INFORMATION: real-time PCR primer for ACTB

<400> SEQUENCE: 27
ggatgccaca ggactccat                                                 19

<210> SEQ ID NO 28
<211> LENGTH: 30
<212> TYPE: DNA
<213> ORGANISM: Artificial Sequence
<220> FEATURE:
<223> OTHER INFORMATION: sequence of control DNAzyme which is not
      complementary to any mRNA in human cells

<400> SEQUENCE: 28
catcggaggc tagctacaac gagacagctg                                     30

<210> SEQ ID NO 29
<211> LENGTH: 15
<212> TYPE: RNA
<213> ORGANISM: Homo sapiens

<400> SEQUENCE: 29
gcucaucacg cagcu                                                     15

<210> SEQ ID NO 30
<211> LENGTH: 15
<212> TYPE: RNA
<213> ORGANISM: Homo sapiens

<400> SEQUENCE: 30
gcucaucaug cagcu                                                     15

<210> SEQ ID NO 31
<211> LENGTH: 17
<212> TYPE: RNA
<213> ORGANISM: Homo sapiens

<400> SEQUENCE: 31
agcucaucac gcagcuc                                                   17

<210> SEQ ID NO 32
<211> LENGTH: 17
```

```
<212> TYPE: RNA
<213> ORGANISM: Homo sapiens

<400> SEQUENCE: 32
agcucaucau gcagcuc                                                  17

<210> SEQ ID NO 33
<211> LENGTH: 17
<212> TYPE: RNA
<213> ORGANISM: Homo sapiens

<400> SEQUENCE: 33 auuugggcu ggccaaa                                                   17

<210> SEQ ID NO 34
<211> LENGTH: 17
<212> TYPE: RNA
<213> ORGANISM: Homo sapiens

<400> SEQUENCE: 34 uuugggcug gccaaac                                                   17

<210> SEQ ID NO 35
<211> LENGTH: 17
<212> TYPE: RNA
<213> ORGANISM: Homo sapiens

<400> SEQUENCE: 35 auuugggcg ggccaaa                                                   17

<210> SEQ ID NO 36
<211> LENGTH: 17
<212> TYPE: RNA
<213> ORGANISM: Homo sapiens

<400> SEQUENCE: 36 uuugggcgg gccaaac                                                   17

<210> SEQ ID NO 37
<211> LENGTH: 17
<212> TYPE: RNA
<213> ORGANISM: Homo sapiens

<400> SEQUENCE: 37
acagauuuug ggcuggc                                                  17

<210> SEQ ID NO 38
<211> LENGTH: 17
<212> TYPE: RNA
<213> ORGANISM: Homo sapiens

<400> SEQUENCE: 38
cagauuuugg gcuggcc                                                  17

<210> SEQ ID NO 39
<211> LENGTH: 17
<212> TYPE: RNA
<213> ORGANISM: Homo sapiens

<400> SEQUENCE: 39
acagauuuug ggcgggc                                                  17

<210> SEQ ID NO 40
```

```
<211> LENGTH: 17
<212> TYPE: RNA
<213> ORGANISM: Homo sapiens

<400> SEQUENCE: 40
cagauuuugg gcgggcc                                                    17

<210> SEQ ID NO 41
<211> LENGTH: 17
<212> TYPE: RNA
<213> ORGANISM: Homo sapiens

<400> SEQUENCE: 41
gauuuggggc uggccaa                                                    17

<210> SEQ ID NO 42
<211> LENGTH: 17
<212> TYPE: RNA
<213> ORGANISM: Homo sapiens

<400> SEQUENCE: 42
gggcuggcca acugcug                                                    17

<210> SEQ ID NO 43
<211> LENGTH: 17
<212> TYPE: RNA
<213> ORGANISM: Homo sapiens

<400> SEQUENCE: 43
gauuuggggc gggccaa                                                    17

<210> SEQ ID NO 44
<211> LENGTH: 17
<212> TYPE: RNA
<213> ORGANISM: Homo sapiens

<400> SEQUENCE: 44
gggcgggcca acugcug                                                    17

<210> SEQ ID NO 45
<211> LENGTH: 17
<212> TYPE: RNA
<213> ORGANISM: Homo sapiens

<400> SEQUENCE: 45
ggcuggccaa cugcugg                                                    17

<210> SEQ ID NO 46
<211> LENGTH: 17
<212> TYPE: RNA
<213> ORGANISM: Homo sapiens

<400> SEQUENCE: 46
ggcgggccaa cugcugg                                                    17

<210> SEQ ID NO 47
<211> LENGTH: 20
<212> TYPE: RNA
<213> ORGANISM: Homo sapiens

<400> SEQUENCE: 47
gucgcuauca aaacaucucc                                                 20
```